US007534774B2

(12) United States Patent
Sosnowski et al.

(10) Patent No.: US 7,534,774 B2
(45) Date of Patent: May 19, 2009

(54) TRAVERSAL OF NUCLEIC ACID MOLECULES THROUGH A FLUID SPACE AND EXPRESSION IN REPAIR CELLS

(75) Inventors: Barbara A. Sosnowski, Coronado, CA (US); Glenn Pierce, Rancho Santa Fe, CA (US)

(73) Assignee: Tissue Repair Company, San Diego, CA (US)

( * ) Notice: Subject to any disclaimer, the term of this patent is extended or adjusted under 35 U.S.C. 154(b) by 0 days.

(21) Appl. No.: 10/264,284

(22) Filed: Oct. 2, 2002

(65) Prior Publication Data

US 2003/0148979 A1    Aug. 7, 2003

Related U.S. Application Data

(60) Provisional application No. 60/327,513, filed on Oct. 3, 2001.

(51) Int. Cl.
A61K 48/00    (2006.01)
A01N 63/00    (2006.01)
(52) U.S. Cl. ........................................ 514/44; 424/93.1
(58) Field of Classification Search ................. 424/93.2
See application file for complete search history.

(56) References Cited

U.S. PATENT DOCUMENTS

| 4,352,883 | A |   | 10/1982 | Lim |
| 4,394,370 | A |   | 7/1983  | Jefferies |
| 4,485,097 | A |   | 11/1984 | Bell |
| 4,505,266 | A |   | 3/1985  | Yannas et al. |
| 4,521,909 | A |   | 6/1985  | Wang |
| 4,596,574 | A |   | 6/1986  | Urist |
| 4,868,116 | A |   | 9/1989  | Morgan et al. |
| 4,963,489 | A |   | 10/1990 | Naughton et al. |
| 4,972,385 | A |   | 11/1990 | Teel |
| 4,975,527 | A |   | 12/1990 | Koezuka et al. |
| 4,980,286 | A |   | 12/1990 | Morgan et al. |
| 5,231,169 | A |   | 7/1993  | Constantz et al. |
| 5,270,300 | A |   | 12/1993 | Hunziker |
| 5,399,346 | A |   | 3/1995  | Anderson et al. |
| 5,502,092 | A |   | 3/1996  | Barrows et al. |
| 5,514,378 | A |   | 5/1996  | Mikos et al. |
| 5,679,338 | A |   | 10/1997 | Yeh et al. |
| 5,716,981 | A |   | 2/1998  | Hunter et al. |
| 5,770,580 | A |   | 6/1998  | Ledley et al. |
| 5,792,453 | A | * | 8/1998  | Hammond et al. ....... 424/93.21 |
| 5,792,751 | A |   | 8/1998  | Ledley et al. |
| 5,859,208 | A |   | 1/1999  | Fiddes et al. ................. 530/399 |
| 5,962,427 | A | * | 10/1999 | Goldstein et al. ............. 514/44 |
| 6,228,423 | B1 |   | 5/2001  | Sokoll et al. |
| 2001/0044413 | A1 | * | 11/2001 | Pierce et al. .................. 514/44 |

FOREIGN PATENT DOCUMENTS

| AU | B-68389/90 | 6/1991 |
| WO | WO 97/00201 | 1/1987 |
| WO | WO 89/05345 | 6/1989 |
| WO | WO 89/07136 | 8/1989 |
| WO | WO 90/11092 | 10/1990 |
| WO | WO 95/19182 | 7/1995 |
| WO | WO 97/38729 | 10/1997 |

OTHER PUBLICATIONS

Doukas et al. Human Gene Therapy 12:783-798, 2001.*
Chandler et al. Molecular Thrapy, 2, 153-160, 2000.*
Chandler et al. Wound Rep. Reg. 2000, 8:473-479.*
Anderson et al., Nature, vol. 392, pp. 25-20, 1998.*
Chvapil (Journal of Biomedical Research, 11: 721-741, 1977).*
Tomasoni, S and A Benigni Current Gene Therapy 4(1):115-122, 2004.*
Gautam, A et al. Am J Respir Med 1(1):35-46. 2002.*
Yang, X Radiology 228:36-49. 2003.*
Amiel et al., "Rib Perichondrial Grafts for the Repair of Full-Thickness Articular-Cartilage Defects," *J. of Bone and Joint. Surgery* 67A(6):911-920, Jul. 1985.
Anseth et al., "Photopolymerizable Degradable Polyanhydrides with Osteocompatibility," *Nature Biotechnology* 17:156-159, Feb. 1999.
Anson et al., "Towards Gene Therapy for Hemophilia B," *Mol. Biol. Med.* 4(1):11-20, Feb. 1987.
Blaese et al., "T Lymphocyte-Directed Gene Therapy for ADA⁻ SCID: Initial Trial Results After 4 Years," *Science* 270:475-480, Oct. 1995.
Elgendy et al., "Osteoblast-Like Cell (MC3T3-E1) Proliferation on Bioerodible Polymers: An Approach Towards the Development of a Bone-Biorodible Polymer Composite Material," *Biomaterials* 14(4):263-269, 1993.
Gailit et al., "Wound Repair in the Context of Extracellular Matrix," *Curr. Opin. In Cell Bio.* 6(5):717-725, 1994.
Langer et al., "Polymers for the Sustained Release of Proteins and Other Macromolecules," *Nature* 263(5580):797-800, Oct. 1976.
Laurencin et al., "use of Polyphosphazenes for Skeletal Tissue Regeneration," *J. of Biomed. Mat. Res.* 27(7):963-973, Jul. 1993.
Ledley F., "Samatic Gene Therapy for Human Disease: Background and Prospects," *J. of Pediatrics* 110(1):1-8, Jan. 1987.
Ledley et al., "Retroviral Gene Transfer into Primary Hepatocytes: Implications for Genetic Therapy of Liver-Specific Functions," *Proc. Natl. Acad. Sci. USA* 84(15):5335-5339, Aug. 1987.

(Continued)

*Primary Examiner*—Deborah Crouch
*Assistant Examiner*—Marcia S Noble
(74) *Attorney, Agent, or Firm*—Seed IP Law Group PLLC

(57) ABSTRACT

Disclosed are methods for use in transferring nucleic acids into cells at a wound site associated with a fluid space. These gene transfer protocols are suitable for use in transferring various nucleic acids into cartilage, cardiac muscle, and other tissues, and have many uses including treating diseases such as arthritis and ischemic heart disease, and promoting wound healing. The invention further disclosed pharmaceutical compositions that may be used in the practice of the invention to transfer the nucleic acid of interest. Such compositions include any multi-partitioned biocompatible matrix in combination with multiple nucleic acids of interest.

3 Claims, 6 Drawing Sheets

OTHER PUBLICATIONS

Lim et al., "Long-Term Expression of Human Adenosine Deaminase in Mice Transplanted with Retro-Virus Infected Hematopoietic Stem Cells," *Proc. Natl. Acad. Sci. USA* 86(22):8892-8896, Nov. 1989.

Morgan et al., "Expression of an Exogenous Growth Hormone Gene by Transplantable Human Epidermal Cells," *Science* 237:1476-1479, Sep. 1987.

Nicolau et al., "In Vivo Expression of Rat Insulin After Intravenous Administration of the Liposome-Entrapped Gene for Rat Insulin I," *Proc. Natl. Acad. Sci. USA* 80(4):1068-1072, Feb. 1983.

Palmer et al., "Efficient Retorvirus-Mediated transfer and Expression of a Human Adenosine Deaminase Gene in Diploid Skin Fibroblasts from an Adenosine Deaminase-Deficient Human," *Proc. Natl. Acad. Sci. USA* 84(4):1055-1059, Feb. 1987.

Pelletier et al., "Are Cytokine Involved in Osteoarthritic Pathophysiology?," *Seminars in Arthritis and Rheumatism* 20(6):12-25, Jun. 1991.

Rosenberg et al., "Grafting Generically Modified Cells to the Damaged Brain: Restorative Effects of NGF Expression," *Science* 242:1575-1578, Dec. 1988.

Wilson et al., "Temporary Amelioration of Hyperlipidemia in Low Density Lipoprotein Receptor-Deficient Rabbits Transplanted with Genetically Modified Hepatocytes," *Proc. Natl. Acad. Sci. USA* 87:8437-8441, Nov. 1990.

Wolff et al., "Expression of Retorvirally transduced genes in Primary Cultures of Adult Rat Hepatocytes," *Proc. Natl. Acad. Sci. USA* 84(10):3344-3348, May 1987.

\* cited by examiner

TRAVERSAL OF NUCLEIC ACID MOLECULES THROUGH A FLUID SPACE AND EXPRESSION IN REPAIR CELLS

TECHNICAL FIELD

The present invention relates to novel methods and compositions for the presentation and direct transfer of nucleic acids encoding agents of interest into mammalian repair cells across a fluid space.

BACKGROUND OF THE INVENTION

Currently available wound healing therapies involve the administration of therapeutic proteins. Such therapeutic proteins may include regulatory factors involved in the normal healing process such as systemic hormones, cytokines, growth factors and other proteins that regulate proliferation and differentiation of cells. Growth factors, cytokines and hormones reported to have such wound healing capacity include, for example, the transforming growth factor-superfamily (TGF) of proteins (Cox, *Cell Biol. Int.* 19:357-371, 1995) acidic fibroblast growth factor (FGF) (Slavin, *Cell Biol. Int.* 19:431-444, 1995), macrophage-colony stimulating factor (M-CSF) and calcium regulatory agents such as parathyroid hormone (PTH).

A number of problems are associated with the use of therapeutic proteins, i.e., cytokines, in wound healing therapies. First, the purification and/or recombinant production of therapeutic proteins is often an expensive and time-consuming process. Despite best efforts, however, purified protein preparations are often unstable making storage and use cumbersome, and protein instability can lead to unexpected inflammatory reactions (to protein breakdown products) that are toxic to the host.

Second, systemic delivery of therapeutic proteins, i.e., cytokines, can be associated with serious unwanted side effects in unwounded tissue. Due to inefficient delivery to specific cells and tissues in the body, administration of high doses of protein are required to ensure that sufficient amounts of the protein reach the appropriate tissue target. Because of the short half life in the body due to proteolytic degradation, the proteins must also be administered repeatedly which may give rise to an immune reaction to the therapeutic proteins. The circulation of high doses of therapeutic proteins is often toxic due to pleiotropic effects of the administered protein, and may give rise to serious side effects.

Third, exogenous delivery of recombinant proteins is inefficient. Attempts have been made to limit the administration of high levels of protein through immobilization of therapeutic protein at the target site. However, this therapeutic approach complicates the readministration of the protein for repeated dosing.

Fourth, for a variety of proteins such as membrane receptors, transcription factors and intracellular binding proteins, biological activity is dependent on correct expression and localization in the cell. For many proteins, correct cellular localization occurs as the protein is post-translationally modified inside the cells. Therefore, such proteins cannot be administered exogenously in such a way as to be taken up and properly localized inside the cell.

As these problems attest, current recombinant protein therapies for wound healing are flawed, because they do not present a rational method for delivery of exogenous proteins. These proteins, e.g., cytokines, are normally produced at their site of action in physiological amounts and efficiently delivered to cell surface signaling receptors.

Gene Therapy

Gene therapy was originally conceived of as a specific gene replacement therapy for correction of heritable defects to deliver functionally active therapeutic genes into targeted cells. Initial efforts toward somatic gene therapy have relied on indirect means of introducing genes into tissues, called ex vivo gene therapy, e.g., target cells are removed from the body, transfected or infected with vectors carrying recombinant genes, and re-implanted into the body ("autologous cell transfer"). A variety of transfection techniques are currently available and used to transfer DNA in vitro into cells; including calcium phosphate-DNA precipitation, DEAE-Dextran transfection, electroporation, liposome mediated DNA transfer or transduction with recombinant viral vectors. Such ex vivo treatment protocols have been proposed to transfer DNA into a variety of different cell types including epithelial cells (U.S. Pat. No. 4,868,116; Morgan and Mulligan WO87/00201; Morgan et al., *Science* 237:1476-1479, 1987; Morgan and Mulligan, U.S. Pat. No. 4,980,286), endothelial cells (WO89/05345), hepatocytes (WO89/07136; Wolff et al., *Proc. Natl. Acad. Sci. USA* 84:3344-3348, 1987; Ledley et al., *Proc. Natl. Acad. Sci.* 84:5335-5339, 1987; Wilson and Mulligan, WO89/07136; Wilson et al., *Proc. Natl. Acad. Sci.* 87:8437-8441, 1990) fibroblasts (Palmer et al., *Proc. Natl. Acad. Sci. USA* 84:1055-1059, 1987; Anson et al., 1987, Mol. Biol. Med. 4:11-20; Rosenberg et al., *Science* 242:1575-1578, 1988; Naughton & Naughton, U.S. Pat. No. 4,963,489), lymphocytes (Anderson et al., U.S. Pat. No. 5,399,346; Blaese, R. M. et al., *Science* 270:475-480, 1995) and hematopoietic stem cells (Lim, B. et al., *Proc. Natl. Acad. Sci. USA* 86:8892-8896, 1989; Anderson et al., U.S. Pat. No. 5,399,346).

Direct in vivo gene transfer has recently been attempted with formulations of DNA trapped in liposomes (Ledley et al., *J. Pediatrics* 110:1, 1987); or in proteoliposomes that contain viral envelope receptor proteins (Nicolau et al., *Proc. Natl. Acad. Sci. U.S.A.* 80:1068, 1983); and DNA coupled to a polylysine-glycoprotein carrier complex. In addition, "gene guns" have been used for gene delivery into cells (Australian Patent No. 9068389). It has even been speculated that naked DNA, or DNA associated with liposomes, can be formulated in liquid carrier solutions for injection into interstitial spaces for transfer of DNA into cells (Felgner, WO90/11092).

Perhaps one of the greatest problems associated with currently devised gene therapies, whether ex vivo or in vivo, is the inability to transfer DNA efficiently into a targeted cell population and to achieve a useful level expression of the gene product in vivo. Viral vectors are regarded as the most efficient system, and recombinant replication-defective viral vectors have been used to transduce (i.e., infect) cells both ex vivo and in vivo. Such vectors have included retroviral, adenovirus and adeno-associated and herpes viral vectors. While highly efficient at gene transfer, the major disadvantages associated with the use of viral vectors include the inability of many viral vectors to infect non-dividing cells; problems associated with insertional mutagenesis; inflammatory reactions to the virus and potential helper virus production, and/or production and transmission of harmful virus to other human patients.

In addition to the low efficiency of most cell types to take up and express foreign DNA, many targeted cell populations are found in such low numbers in the body that the efficiency of presentation of DNA to the specific targeted cell types is even further diminished. At present, no protocol or method, currently exists to increase the efficiency with which DNA is targeted to the targeted cell population.

Accordingly, there is a need in the art for efficiently transferring nucleic acids into a targeted cell population and to achieve high level expression of the transferred nucleic acids in vivo.

Fluid Space

Cells and tissues of the body are composed of and surrounded by fluids. Body fluids include both intracellular and extracellular fluids. Intracellular fluids are body fluids that are within the cell membranes. Generally, intracellular fluids are composed of water and dissolved solutes. Extracellular fluids include body fluids outside of cells, such as interstitial fluid, plasma, lymph, cerebrospinal fluid, etc. Extracellular fluids consist of ultrafiltrates of the blood plasma and transcellular fluid that is produced by active cellular secretion. Extracellular fluids provide a constant external environment for cells. Interstitial fluid is a type of extracellular fluid that bathes the cells of most tissues but is not within the confines of the blood or lymph vessels and is not a transcellular fluid. Interstitial fluid is formed by filtration through the blood capillaries and is drained away as lymph. Examples of interstitial fluids include allantoic fluid, amniotic fluid, ascitic fluid, follicular fluid, pericardial fluid, seminal fluid, and synovial fluid.

Extracellular fluids generally accumulate in fluid spaces, which includes any space or cavity capable of containing fluid. It is not necessary for fluid spaces to actually contain fluid. Fluid spaces that do not contain fluid are referred to histologically as "potential spaces." Examples of fluid spaces include follicles of the thyroid, joint cavities, tendon sheaths, the vitreous of the eye, the four ventricles of the brain, the subarachnoid space, the articular space, the inner and middle ear, the central canal of the spinal cord, the pericardium, the peritoneal cavity, pleural cavity, and retroperitoneal cavity. Blood vessels such as veins, arteries and capillaries are not considered fluid spaces.

Efforts to perform gene therapy on tissues associated with fluid spaces include the introduction of a gene therapy vector directly into a fluid space under conditions in which cells associated with the fluid space can incorporate the nucleic acid vector (Ledley and O'Malley, U.S. Pat. No. 5,792,751). These methods generally rely on the ability of target tissues directly in contact with a fluid space to take up introduced nucleic acids by pinocytosis, phagocytosis, receptor mediated uptake, or membrane fusion. In addition, these methods depend upon the ability of the transduced tissues to express the product of the introduced gene therapy vector. Accordingly, vectors capable of tissue specific expression are necessary to direct expression in defined tissues of interest. Another drawback of the methodology described by Ledley is that the introduction of DNA expression vectors directly into a fluid space requires diffusion to the site of treatment as well as requiring liquid formulations, which may require refrigeration and associated sterile techniques.

SUMMARY OF THE INVENTION

The present invention provides generally for methods for transferring a nucleic acid molecule into cells associated with a fluid space, comprising contacting a wound site with a composition comprising a nucleic acid molecule and a biocompatible matrix, the wound site being situated in a tissue associated with the fluid space.

In certain embodiments of the method, the tissue may be cartilage, bone/cartilage interface, or cardiac muscle.

In further embodiments of the method, the wound is a wound that may be induced by injury, a disease state, or is an iatrogenic wound.

In one embodiment of the present method, the contacting process comprises bringing the nucleic acid molecule into contact with the biocompatible matrix to form a matrix-nucleic acid composition and bringing the matrix-nucleic acid composition into contact with the tissue site.

In a particular embodiment, the nucleic acid molecule may be a DNA molecule, an RNA molecule, an antisense nucleic acid molecule, a linear nucleic acid molecule, a plasmid or a recombinant insert with the genome of a recombinant virus. In a further embodiment of the present invention, the DNA molecule comprises a promoter operably linked to a sequence encoding a gene product.

In an additional embodiment, the biocompatible matrix is a biological matrix. In yet a further embodiment, the biological matrix comprises a polymer. In certain embodiments, the biological matrix may consist of collagen, type I collagen, type II collagen, mineralized collagen, atelocollagen, purified proteins, purified peptides, polysaccharides, or extracellular matrix compositions. In one embodiment, the polysaccharides may be any one of chitosan, alginate, dextran, hyaluronic acid, or cellulose.

In a further embodiment of the method, the biocompatible matrix is a synthetic matrix. In an additional embodiment, the synthetic matrix may comprise a polymer. In yet a further embodiment, the polymer may be any one of polyethylene glycols and their derivatives, polyesters, polyethers, polyanhydrides, polyalkylcyanoacrylates, polyacrylamides, polyorthoesters, polyphospazenes, polyvinylacetates, block copolymers, polytetrafluoroethylene (PTFE), and polyurethanes.

In certain embodiments, the polymer may comprise lactic acid, glycolic acid, or a copolymer that may comprise lactic acid and glycolic acid (PLGA).

In an additional embodiment, the biocompatible matrix may be biodegradable or non-biodegradable. In a further embodiment, the non-biodegradable matrix may comprises any one of various polymers including poly(dimethysiloxane) and poly(ethylene-vinyl acetate). In yet a further embodiment, the biocompatible matrix is a collagen, metal, hydroxyapatite, bioglass, aluminate, bioceramic materials, hyaluronic acid polymers, acrylic ester polymer, lactic acid polymer, glycolic acid polymer, lactic acid/glycolic acid polymer, purified proteins, purified peptides, or extracellular matrix compositions.

In an additional embodiment, the DNA molecule of the present method encodes a therapeutic protein. In another embodiment, the growth factor may be any one of numerous factors including a transforming growth factor (TGF), a fibroblast growth factor (FGF), a platelet derived growth factor (PDGF), an insulin like growth factor (IGF), a hepatocyte growth factor (HGF), an epidermal growth factor (EGF), a connective tissue growth factor (CTGF), a bone morphogenetic factor (BMP), or a cartilage-derived morphogenic protein (CDMP).

In one embodiment, the therapeutic protein is a hormone, such as a growth hormone. In an additional embodiment, the growth hormone is human parathyroid hormone (PTH).

In an additional embodiment, the therapeutic protein may be any one of TGF, FGF, PDGF, IGF, HGF, EGF, CTGF, BMP, CDMP, latent TGF-β binding protein (LTBP), keratinocyte growth factor (KGF), vascular endothelial growth factor (VEGF), Factor VIII, Factor IX, erythropoietin (EPO), tissue plaminogen activator (TPA), leukemia inhibitory factor (LIF), parathyroid hormone-related peptide (PTHrP), activin, inhibin, interleukin, macrophage-colony stimulating factor (M-CSF), granulocyte macrophage-colony stimulating factor (GM-CSF), skeletal growth factor (SGF), chondromodulin, therapeutic mono or polyclonal antibodies and fragments thereof, enzymes involved in production/processing of collagen (for example, procollagen N-proteinase and procollagen C-proteinase), enzymes that make hyaluronic acid, transcriptions factors that trigger proliferation, differentiation, and morphogenic pathways, cell survival factors such as BCL-2, or cell death factors such as the Ras superfamily of low-molecular-weight GTPases.

One aspect of the present invention provides a method of stimulating gene expression in cartilage progenitor cells located within a cartilage progenitor tissue site of an animal, comprising contacting the tissue site with a composition comprising a chondrogenic gene and a biocompatible matrix.

In one embodiment, expression of the gene in the cells stimulates the cells to promote cartilage tissue repair or regeneration.

In an additional embodiment, the contacting process comprises bringing the chondrogenic gene with the biocompatible matrix to form a matrix-gene composition and bringing the matrix-gene composition into contact with the tissue site. In a further emobidment, the chondrogenic gene may be in the form of plasmid DNA, a DNA insert within the genome of a recombinant adenovirus, a DNA insert within the genome of a recombinant adeno-associated virus (AAV) or a DNA insert within the genome of a recombinant retrovirus. In yet another embodiment, the chondrogenic gene may be a parathyroid hormone (PTH) gene, a bone morphogenetic protein (BMP) gene, a cartilage-derived morphogenic protein (CDMP) gene, a growth factor gene, a growth factor receptor gene, a fibroblast growth factor (FGF) gene, an IGF gene, an HGF gene, a gene in the TGF family of genes, a PDGF gene, an EGF gene, a LIF gene, a PTHrP gene, a CTGF gene, a SGF gene, a BIP gene, a MP52 gene, and a chondromudulin gene.

In a particular embodiment, the chondrogenic gene may be a basic FGF gene, an IGF-I or IGF-II gene, a TGFα, TGFβ1 or TGFβ2 gene, BMP2, BMP3, BMP4, BMP5, BMP6, BMP7, BMP8, BMP9, BMP10, BMP11, BMP12, or BMP13 genes.

In an additional embodiment, the growth factor receptor gene is an IGF receptor gene or a MBP receptor gene.

In a further embodiment, the biocompatible matrix is a collagenous, polyethylene, poly(vinyl alcohol) hydrogel, polyethylene glycol, methyl cellulose, hydroxyapatite, acrylic ester polymer, lactic acid polymer, glycolic acid polymer, reconstituted fibrin-thrombin gels, anhydride polymer, orthoester polymer, hyaluronan, fibrin, carbon fiber, tetrafluoroethylene polymer, polyester, or lactic acid/glycolic acid polymer matrix.

In one particular embodiment, the biocompatible matrix is a collagen preparation. In another embodiment, the biocompatible matrix may be hydroxyapatite matrix, a lactic acid polymer matrix, or a fibrin matrix.

In an additional embodiment, the cartilage progenitor tissue site is a site of cartilage injury.

In yet another embodiment, the cartilage injury is a partial-thickness injury or a full-thickness injury.

In a further embodiment, the cartilage progenitor tissue site is a cartilage cavity site or may be the result of surgery or the removal of a cartilage tumor An additional aspect of the present invention provides a method of stimulating cartilage repair or regeneration comprising implanting at a cartilage defective site a matrix-gene composition comprising a chondrogenic gene and a biocompatible matrix.

In one embodiment of the method, the matrix comprises a first portion and a second portion. In an additional embodiment, the first portion comprises a gene to stimulate cartilage growth and the second portion comprises a gene to stimulate bone growth.

Another aspect of the present invention provides a method of treating arthritis comprising implanting at a cartilage defective site a matrix-gene composition comprising a chondrogenic gene and a biocompatible matrix. In one embodiment, the chondrogenic gene is an IL-4 gene. In further embodiments, the chondrogenic gene encodes a ribozyme that cleaves mRNAs for an inflammation mediator, an antisense nucleic acid that binds to an mRNA for an inflammation mediator. In an additional embodiment, the inflammation mediator may be interleukin-1 (IL-1), IL-6, IL-8, tumor necrosis factor α (TNFα), or GM-CSF. In a further embodiment, the matrix-gene composition may encode a soluble receptor or antibody, or antibody fragment thereof, that binds to a mediator of inflammation.

In another embodiment, the chondrogenic gene is in the form of plasmid DNA, a DNA insert within the genome of a recombinant adenovirus, a DNA insert within the genome of a recombinant adeno-associated virus (AAV) or a DNA insert within the genome of a recombinant retrovirus. In an additional embodiment, the chondrogenic gene may be a PTH gene, a BMP gene, a CDMP gene, a growth factor gene, a growth factor receptor gene, an FGF gene, an IGF gene, an HGF gene, a TGF gene, a PDGF gene, an EGF gene, a LIF gene, a PTHrP gene, and a CTGF gene, a SGF gene, a BIP gene, a MP52 gene, or a chondromodulin gene.

In one particular embodiment, the chondrogenic gene is a basic FGF gene. In a further embodiment, the chondrogenic gene is an IGF-I or IGF-II gene. In yet a further embodiment, the chondrogenic gene may be a TGFα, TGFβ1 or TGFβ2 gene. In another embodiment, the chondrogenic gene may be any of a number of genes, including the BMP2, BMP3, BMP4, BMP5, BMP6, BMP7, BMP8, BMP9, BMP10, BMP11, BMP12, BMP13 genes.

In an additional embodiment, the biocompatible matrix is a collagenous, polyethylene, poly(vinyl alcohol) hydrogel, polyethylene glycol, methyl cellulose, hydroxyapatite, acrylic ester polymer, lactic acid polymer, glycolic acid polymer, reconstituted fibrin-thrombin gels, anhydride polymer, orthoester polymer, hyaluronan, fibrin, carbon fiber, tetrafluoroethylene polymer, polyester, or lactic acid/glycolic acid polymer matrix.

In one particular embodiment, the biocompatible matrix is a collagen preparation. In yet another embodiment, the biocompatible matrix is a hydroxyapatite matrix. In a further embodiment, the biocompatible matrix is a lactic acid polymer matrix. In still a further embodiment, the biocompatible matrix is a fibrin matrix.

An additional aspect of the present invention provides a method of treating ischemic heart disease comprising implanting a matrix-gene composition comprising an angiogenic gene and a biocompatible matrix into an ischemic region.

In one embodiment of the method, the angiogenic gene is an FGF gene, a VEGF gene, a TGF gene, a TNFα gene, an HGF gene, a PDGF gene, or a gene encoding a transcription factor.

In an additional embodiment, the biocompatible matrix is a collagen, hydroxyapatite, lactic acid polymer, or fibrin matrix.

Another aspect of the present invention provides a composition comprising multiple genes associated with a multi-partitioned biocompatible matrix.

DETAILED DESCRIPTION OF THE INVENTION

Figure 1:
FIG. 1 shows 3 panels: the left panel is a section stained with Alcian blue, and the right 2 panels are Formalin-fixed, paraffin-embedded sponge sections stained using Masson's Trichrome. PVA sponges were implanted subcutaneously into rats on day 0 and injected on day 4 with collagen containing $10^9$ pfu adenovirus encoding luciferase (AdLuc) or PDGF-BB (AdPDGF). At day 4, this is a fluid filled space. At day 10 post-implantation, sponges were removed and processed. Image-Pro Plus software (Media Cybernetics, Silver Spring, Md.) was used to differentiate new tissue from sponge matrix based on pixel density.
Figure 1:
Figure 1:

Prior to setting forth the invention, it may be helpful to an understanding thereof to set forth definitions of certain terms that will be used hereinafter.

A "nucleic acid molecule," as used herein, refers to a polynucleotide molecule in the form of a separate fragment or as a component of a larger nucleic acid construct, that has been separated from its source cell (including the chromosome it normally resides in) at least once in a substantially pure form. Nucleic acid molecules may be comprised of a wide variety of nucleotides, including DNA, RNA, nucleotide analogues, or some combination of these.

A "gene-activated matrix (GAM)" is used herein to refer to any biocompatible matrix containing a nucleic acid (or nucleic acids) encoding a therapeutic agent of interest. For example, gene-activated matrices are placed within wound sites in the body of a mammalian host to enhance wound healing.

A "repair cell" is defined herein as any cell that is stimulated to migrate and proliferate in response to tissue injury. Repair cells are a component of the wound healing response. Such cells include macrophages, lymphocytes, epithelial cells, fibroblasts, capillary endothelial cells, capillary pericytes, mast cells, megakaryocytes, keratinocytes, smooth muscle cells, mononuclear inflammatory cells, segmented inflammatory cells, granulation tissue cells, tissue specific cells and their precursors, including but not limited to hepatocytes, cardiac myocytes, renal tubular cells, type II pneumocytes, keratinocytes, intestinal cells, gastric cells, chnondroblasts, osteoblasts, and the like.

A "wound site" is defined as any location in the host that arises from traumatic tissue injury, from a disease state, or from tissue damage either induced by, or resulting from, medical procedures including injection or suturing or similar procedures.

A "biocompatible matrix," as used herein, refers to virtually any composition or substance, including both biological (natural) and synthetic components so long as the substance is capable of coexistence with living tissues or organisms without causing undue harm (e.g., artificial joint compositions, PLGA, etc.). A biocompatible matrix may comprise an interior and exterior surface (e.g., a catheter, hollow fibers, pores, etc.), wherein the interior surface of the matrix is capable of supporting cellular ingrowth and, accordingly, is capable of being accessed by biological material (e.g., fluid and cells) of the surrounding environment. A biocompatible matrix may also be any enclosure or compartment capable of being infiltrated by cells. Such an enclosure or compartment may be composed of a porous material or membrane through which living cells can migrate. Typically, the biocompatible matrix will also be a polymer. Such polymers should possess appropriate mechanical and physical properties; tissue, cell, and blood compatibility (minimum histotoxicity, noncarcinogenicity); appropriate aging properties in the implant site (stability or degradability); and capable of being produced in a sterile fashion.

"Cellular infiltration", as used herein, refers to cell migration in reference to a biocompatible substance. Cellular infiltration encompasses cell migration into and along the interior surface of a biocompatible substance such as a matrix. Cellular infiltration also includes cell migration across a permeable biocompatible substance. For example, cell infiltration describes cell migration across a permeable biocompatible membrane into a space or compartment enclosed by the membrane (see, e.g, Cell Encapsulation Technology and Therapeutics, (Kuhtreiber, Langer, Chick (eds.), Birkhauser, Boston, 1999).

A "chondrocyte progenitor cell," as used herein, refers to a pluripotent, or lineage-uncommitted, progenitor cell that is potentially capable of an unlimited number of mitotic divisions to either renew its line or to produce progeny cells that will differentiate into chondrocytes. This cell is typically referred to as a "stem cell" or "mesenchymal stem cell" in the art. Alternatively, a "chondrocyte progenitor cell" is a lineage-committed progenitor cell produced from the mitotic division of a stem cell that will eventually differentiate into a chondrocyte. The lineage-committed progenitor cell is generally incapable of an unlimited number of mitotic divisions and will eventually differentiate into a chondrocyte. Chondrocyte progenitor cells may come from the synovium or bone marrow, if the subchondral bone plate is penetrated, or other tissues.

A "chondrocyte progenitor tissue site" refers to any tissue site wherein a chondrocyte progenitor cell is located.

The term "chondrogenic gene" is understood to mean any nucleic acid molecule operably linked to a promoter that encodes an RNA molecule, a peptide, a polypeptide, or a protein that has the ability to stimulate chondrocyte progenitor cells to differentiate into chondrocytes or promote the cartilage growth, cartilage repair, cartilage regeneration, or cartilage matrix production. Alternatively, a chondrogenic gene refers to a gene encoding an RNA molecule, a peptide, a polypeptide, or a protein that inhibits, decreases, or prevents cartilage degradation or degeneration.

The term "cartilage repair" refers to restoring damaged cartilage with new tissue that resembles, but does not necessarily replicate the structure, composition, or function of normal cartilage.

The term "cartilage regeneration" refers to forming new tissue that is indistinguishable from normal cartilage, including the zonal organization, composition, and mechanical properties of normal cartilage.

A "fluid space" refers to an extracellular space that is capable of containing fluid (e.g., a potential space). For example, the fluid space can be a pericardial cavity, or formed by the synovium of the joint such as in knee, wrist or spinal cord, by vitreous of the eye or the inner or middle ear, or by peritoneum or pleura of the lung.

A "tissue associated with a fluid space" refers to any tissue surrounding or contacting a fluid space. For instance, the tissue associated with the fluid space in a joint may include synovial membranes, cartilage tissues, and bone tissues.

A "cell associated with a fluid space" refers to any cell located within a tissue surrounding or contacting a fluid space or directly contacting a fluid space. Thus, cells associated with a fluid space include repair cells capable of migrating within or across a fluid space and repair cells which infiltrate a biocompatible matrix located within a tissue associated with a fluid space. A "cell associated with a fluid space" also refers to any cell or tissue adjacent to or neighboring a fluid space. Thus, a "cell associated with a fluid space" is not limited to cells within the tissue enclosing the fluid space. It includes cells contacting or adjacent to cells or tissue defining a fluid space.

A "therapeutic protein" refers to any peptide, polypeptide, or protein that has the capacity to promote wound healing, tissue repair, or tissue regeneration. A therapeutic protein also includes any other peptide, polypeptide, or protein that treats, prevents, or lessens the symptoms or prognosis of any clinical disease, disorder or related biological manifestation.

An "iatrogenic wound" refers to a wound that is either induced by, or results from a medical procedure (e.g., injection, incision, puncture, osteotomy, excision, etc.).

A "diagnostic agent" as used herein, refers to any agent, preferably a polypeptide or a nucleic acid, whose delivery to a cell can be used for diagnostic purposes.

The present invention relates to ex vivo and in vivo methods for presentation and transfer of nucleic acids into mammalian repair cells for the purpose of expressing desired agents such as therapeutic or diagnostic agents. The method of the invention involves implanting or placing a gene-activated matrix into a wound site situated in a tissue associated with a fluid space, typically by traversing the fluid space with the gene-activated matrix or a delivery device for applying the gene-activated matrix. Such delivery devices include, but are not limited to, arthroscopes, catheters, hypodermic needles, etc. Repair cells migrate into the GAM, wherein they take up and express polypeptides or nucleic acids encoded by the DNA. Generally, the expressed polypeptides are secreted by the transduced repair cells and provide a therapeutic effect to the tissue containing the GAM. Expressed nucleic acids may exert an indirect therapeutic effect on the tissue containing the GAM by inducing the transduced repair cells to produce a therapeutic polypeptide.

Wound healing is usually a coordinated, stereotyped sequence of events that includes (a) tissue disruption and loss of normal tissue architecture; (b) cell necrosis and hemorrhage; hemostasis (clot formation); (c) infiltration of segmented and mononuclear inflammatory cells, with vascular congestion and tissue edema; (d) dissolution of the clot as well as damaged cells and tissues by mononuclear cells (macrophages) (e) formation of granulation tissue (fibroplasia and angiogenesis); (f) regeneration of original tissue. This sequence of cellular events has been observed in wounds from all tissues and organs generated in a large number of mammalian species (Gailet et al., Curr. Opin. Cell. Biol. 6:717-725, 1994). Therefore, the cellular sequence described above is a nearly universal aspect of the repair of most mammalian tissues.

The invention is based on the discovery that repair cells involved in the wound healing process will naturally proliferate and migrate to the site of tissue injury and acquire nucleic acid molecules from the gene-activated matrix. Surprisingly, these repair cells, which are normally difficult to efficiently transfect, either in vitro or in vivo, are extremely efficient at taking up and expressing nucleic acids when activated to proliferate by the wound healing process.

Taking advantage of this feature, the methods of the present invention are designed to efficiently transfer one or more nucleic acid molecules encoding therapeutic agents to the proliferating repair cells. The methods involve the administration of a nucleic acid-activated matrix containing nucleic acids, such as RNA molecules or DNA molecules encoding translational products (i.e., therapeutic proteins) or transcriptional products (i.e., antisense or ribozymes) within a mammalian host at the wound site situated in a tissue associated with a fluid space. The wound may arise from traumatic tissue injury, from a disease state, or from tissue damage either induced by, or resulting from, medical procedures.

As the proliferating repair cells migrate to the wound site and contact the gene-activated matrix, wherein they acquire the nucleic acid of interest and thereby amplify the amount of the therapeutic agent, protein or RNA. The transfected repair cells thereby serve as local bioreactors producing therapeutic agents that influence the local repair environment. For example, growth factors or cytokines produced by the transfected repair cells, will bind and stimulate targeted effector cells that express cognate cell surface receptors, thereby stimulating and amplifying the cascade of physiological events normally associated with the wound healing process.

Expression in a localized area should allow for superior biological processes. For example, the presence of multiple cell types (leukocytes, fibroblasts, endothelial cells) within wound repair cell populations would allow for the development of cytokine networks, in which multiple factors produced by diverse cell types induce complex and multifactorial repair processes. Such responses would not be easily achieved if gene transfer were primarily to a single stromal cell type, which would have a limited repertoire of potential cellular activities as compared to the multiple and diverse cell populations present at a wound repair site. Transgene expression by wound repair cells would also allow for the use of non-secreted factors dependent upon intracellular expression for their activity, such as transcription factors, cellular receptors, and cellular adhesion molecules. If these non-secreted factors are to enhance tissue repair, they must be expressed within the repair cell populations, not within stromal cells. Therefore, as a result of their ability to target gene delivery to wound repair cells, GAMs are better suited than aqueous-based gene formulations for limiting further damage to and inducing repair of ischemic and infarcted tissues.

Alternatively, the repair cells may take up and express nucleic acids encoding proteins that inhibit the activity of antagonists of the wound healing process. The nucleic acid molecules may also be antisense or ribozyme RNA molecules that may be used to inhibit translation of mRNAs encoding inflammatory proteins or other factors that inhibit wound healing or cause excessive fibrosis.

The nucleic acid-activated matrix of the invention can be transferred to the patient using a variety of techniques. For example, when stimulating wound healing and regeneration, the matrices are transferred directly to the site of the wound, i.e., the fractured bone, injured connective tissue, ischemic tissue, etc. For use in organ regeneration or angiogenesis, the matrices will typically be surgically placed in a wound made in the organ or tissue site of interest. Since target tissues are associated with a fluid space, preferred methods of the invention introduce gene-activated matrices by traversing the fluid space.

The method of the invention is based on the natural migration and proliferation of repair cells into a wound site and acquisition of nucleic acid molecules from the gene-activated matrix located at the wound site. Therefore, it is understood that the matrices must be transferred into a site in the body where the wound healing process has been induced.

Direct plasmid DNA transfer from a matrix to a mammalian repair cell, through stimulation of the wound healing process, offers a number of advantages. First, the ease of producing and purifying DNA constructs compares favorably with traditional protein production method cost. Second, matrices can act as structural scaffolds that, in and of themselves, promote cell ingrowth and proliferation. Thus, they facilitate the targeting of repair cells for gene transfer. Third, direct gene transfer may be an advantageous method of drug delivery for molecules that normally undergo complex biosynthetic processing or for receptors that must be properly positioned in the cellular membrane. These types of molecules would fail to function properly if exogenously delivered to cells.

The present invention also relates to pharmaceutical compositions comprising matrices containing nucleic acids for use in delivering nucleic acid molecules to a wound site associated with a fluid space. In the various embodiments, the compositions of the invention are comprised of genes of interest associated with a biocompatible matrix material. In certain embodiments, the invention comprises a single nucleic acid molecule, while in other embodiments, the invention comprises multiple nucleic acid molecules. The matrix may or may not be partitioned. In certain embodiments, the matrix contains partitions capable of containing different nucleic acid molecules in discrete compartments or regions. In other embodiments, one or more compartments or regions of a multi-partitioned matrix contain nucleic acid molecules, while one or more other compartments of the multi-partitioned matrix contain polypeptides or proteins. Any number of different nucleic acid molecules or proteins are within the scope of the current invention.

The methods and compositions of the current invention are utilized to introduce therapeutic compounds to body tissues that are associated with fluid spaces. The targeting of tissues associated with fluid spaces offers several advantages. First, the introduction of a biocompatible matrix of the invention to tissues associated with a fluid space results in less damage to surrounding tissues during introduction. The biocompatible matrix may be implanted through or across the fluid space without harming other tissues. The methods of the invention, therefore, are minimally invasive means of utilizing gene therapy to introduce therapeutic molecules to tissues associated with fluid spaces. Additionally, the proximity of a fluid space facilitates the migration of repair cells to the biocompatible matrix that is inserted into a tissue associated with a fluid space. Thus, the methods and compositions of the invention are an efficient means of introducing gene therapy products to target cells associated with a fluid space.

The invention overcomes shortcomings specifically associated with current gene therapy for fluid space related applications. First, direct gene transfer is a rational strategy that allows transfected cells to (a) make physiological amounts of therapeutic protein, modified in a tissue- and context-specific manner, and (b) deliver this protein to the appropriate cell surface signaling receptor under the appropriate circumstances. Exogenous delivery of such molecules is expected to be associated with significant dosing and delivery problems. Delivery via a gene-activated matrix takes advantage of the ability of repair cells to take up nucleic acids and allows administered nucleic acids to be directed to the target tissue. Second, repeated administration, while possible, is not required with gene-activated matrix technology: cell uptake of nucleic acid can be controlled precisely with well-established sustained release delivery technologies, or, alternatively, integration of transfected DNA can be associated with long term recombinant protein expression. Another significant advantage of the current invention is that a single gene therapy vector capable of substantial expression in repair cells may be constructed and used to target a wide variety of tissues associated with a fluid space, since it is predominantly repair cells infiltrating the gene-activated matrix that are transduced. According to the Ledley and O'Malley ('751) invention, however, vectors capable of different tissue specific expression may be required for different target tissues, since the nucleic acids are taken up by cells of the target tissue. However, this is not necessarily required in the present invention.

Matrices

In one aspect of the invention, compositions are prepared in which the nucleic acid encoding the therapeutic agent of interest is associated with or impregnated within a matrix to form a gene-activated matrix. The matrix compositions function (i) to allow ingrowth of repair cells (targeting); and (ii) to harbor nucleic acids (delivery). Once the gene-activated matrix is prepared, it is stored for future use or placed immediately at the site of the wound.

The type of matrix that may be used in the compositions, devices and methods of the invention is virtually limitless and may include both biological and synthetic matrices. The matrix will have all the features commonly associated with being "biocompatible", in that it is in a form that does not produce an adverse, allergic or other untoward reaction when administered to a mammalian host. Such matrices may be formed from either natural and/or synthetic materials. The matrices may be non-biodegradable in instances where it is desirable to leave permanent structures in the body; or biodegradable where the expression of the therapeutic protein is required only for a short duration of time. The matrices may take the form of sponges, implants, tubes, telfa pads, band-aids, bandages, pads, lyophilized components, gels, patches, powders or nanoparticles. In addition, matrices can be designed to allow for sustained release of the nucleic acid over prolonged periods of time while also allowing repair cell in-growth.

The choice of matrix material will differ according to the particular circumstances and the site of the wound that is to be treated. Matrices such as those described in U.S. Pat. No. 5,270,300, incorporated herein by reference, may be employed. Physical and chemical characteristics, such as, e.g., biocompatibility, biodegradability, strength, rigidity, interface properties and even cosmetic appearance may be considered in choosing a matrix, as is well known to those of skill in the art. Appropriate matrices will both deliver the nucleic acid molecule and also act as an in situ scaffolding through which mammalian repair cells may migrate.

An overarching principal of the present invention is that the matrix compositions are capable of supporting cellular ingrowth and harboring nucleic acid molecules and/or proteins that promote tissue growth or cellular proliferation/migration. One of ordinary skill in the art can readily determine whether a particular matrix is capable of cell ingrowth. At a minimum, the matrix must have chambers, pores, or openings large enough for a cell to enter. Such ingrowth can be analyzed by several methodologies, including seeding the matrix ex vivo and growing cells in culture on the matrix and subsequently analyzing the matrix for ingrowth. In addition, the matrix may be implanted in an animal, such as mouse, for a time sufficient to induce ingrowth. The matrix may then be removed and subjected to histological or microscopic analysis to determine the extent of cellular ingrowth. In particular embodiments, ingrowth is initiated via a wound response. While the wound itself may be iatrogenic (e.g., caused directly or indirectly by a physician) or due to pathology or traumatic injury, its source is unimportant as long as wound response is ongoing or initiated at the site of matrix placement.

Matrices have been utilized for a number of years within the context of tissue engineering. However, the present invention utilizes such matrices within the novel context of nucleic acid delivery to cells to achieve nucleic acid delivery to cells associated with fluid spaces. Accordingly, the present invention can utilize those matrix compositions and formulations that have demonstrated utility in tissue engineering. As the matrix need only support nucleic acid association (e.g., impregnation, adsorption, absorption, or chemical conjugation), and permit cell ingrowth, the type of matrix that may be used in the compositions, devices and methods of the invention is virtually limitless and may include both biological and synthetic matrices. In one particular aspect of the invention, compositions are prepared in which the nucleic acid encoding the therapeutic agent of interest is associated with or impregnated within a matrix to form a multi-faceted gene-activated matrix.

Matrices, within the context of the present invention, comprise features commonly associated with being biocompatible when administered to a mammalian host. Matrices may be formed from either natural and/or synthetic materials. The matrices may be non-biodegradable in instances where it is desirable to leave permanent structures in the body, such as an implant; or biodegradable where the expression of the bioactive agent is required only for a short duration of time. The matrices may take the form of sponges, implants, tubes, telfa pads, band-aids, bandages, pads, lyophilized components, gels, patches, powders, porous compositions, or nanoparticles. In addition, matrices can be designed to allow for sustained release of the nucleic acid over prolonged periods of time. In certain embodiments, the matrix of the present invention is flexible and elastic, and may be described as a semisolid scaffold that is permeable to substances such as cells, inorganic salts, aqueous fluids and dissolved gaseous agents including oxygen.

One of ordinary skill in the art understands that the choice of matrix material may differ according to the particular purpose for treatment and the site of matrix placement. Briefly, if a short term indication is to be treated a biodegradable matrix may be more advantageous, while if longer term therapy is envisioned, a non-biodegradable matrix or coated device may be more appropriate. Matrices such as those described in U.S. Pat. Nos. 5,270,300; 5,514,378; 5,502,092 and in "Synthetic Biodegradable Polymer Scaffolds", Atala and Mooney (eds.) Birkhäuser, Boston, USA, 1997; Domb et al., *Polymers for Advanced Technologies* 3:279-292, 1992; "Biodegradable Polymers as Drug Delivery Systems", Chasin and Langer (eds.) Vol. 45 of Drugs and the Pharmaceutical Sciences, M. Dekker, New York, 1990; and the Handbook of Biodegradable Polymers, Domb, Kost, and Wiseman eds., Harwood Academic Publishers, Netherlands, 1997, incorporated herein by reference, in their entirety, may be employed. Physical and chemical characteristics, such as, e.g., biocompatibility, biodegradability, strength, rigidity, interface properties and even cosmetic appearance may be considered in choosing a matrix, as is well known to those of skill in the art. Where the matrices are to be maintained for extended periods of time, non-biodegradable matrices may be employed, such as sintered hydroxyapatite, bioglass, aluminates, other bioceramic materials and metal materials, particularly titanium. A suitable ceramic delivery system is that described in U.S. Pat. No. 4,596,574, incorporated herein by reference. The bioceramics may be altered in composition, such as in calcium-aluminate-phosphate; and they may be processed to modify particular physical and chemical characteristics, such as pore size, particle size, particle shape, and biodegradability. Polymeric matrices may also be employed, including acrylic ester polymers and lactic acid polymers, as disclosed in U.S. Pat. Nos. 4,521,909, and 4,563,489, respectively, each incorporated herein by reference. Particular examples of useful polymers are those of orthoesters, anhydrides, propylene-cofumarates, or a polymer of one or more α-hydroxy carboxylic acid monomers, e.g., α-hydroxy auric acid (glycolic acid) and/or α-hydroxy propionic acid (lactic acid), nylon (polyamides), dacron (polyesters), polystyrene, polypropylene, polyacrylates, polyvinyl compounds (e.g., polyvinylchloride), polycarbonate (PVC), polyethylene (PE), polyethylene glycols (PEG) and their derivatives (including but not limited to cetomacrogol, hydrogel, nonoxynol, octoxynol, poloxalene, poloxamer, polyhydroxyethyl methacrylate, and polysorbates), polypropylene (PS), styrene-acrylonitrile copolymer (SAN), polytetrafluorethylene (PTFE, teflon), thermanox (TPX), and a variety of polyhydroxyalkanoates.

One aspect of the present invention is the use of the matrix in connection with implants and interfaces (e.g., artificial joints), including implants themselves and functional parts of an implant, for example, surgical screws, pins, and the like. In preferred embodiments, it is contemplated that the metal surface or surfaces of an implant or a portion thereof, such as a titanium surface, will be coated with a material that has an affinity for nucleic acids, such as hydroxyl apatite, and then the coated-metal will be further coated with the gene or nucleic acid that one wishes to transfer. The available chemical groups of the absorptive material, such as hydroxyl apatite, may be readily manipulated to control its affinity for nucleic acids, as is known to those of skill in the art.

A biodegradable matrix is generally defined as one that is capable of being reabsorbed into the body. Potential biodegradable matrices for use in connection with the compositions, devices and methods of this invention include, for example, biodegradable and chemically defined calcium sulfate, tricalciumphosphate, hydroxyapatite, polydihydropyrans, polyphosphazenes, poly(ortho esters), polycyanoacrylates, polyanhydrides, polydepsipeptides, aliphatic polyesters (e.g., polyglycolic acid, polylactic acid, copolymers thereof), matrices of purified proteins (e.g., collagen, fibrin, etc.), matrices of purified peptides, polysaccharides (e.g., cellulose, methyl cellulose, starch, chitin, etc.) and semi-purified extracellular matrix compositions.

Preferred biocompatible biodegradable matrices that may be used are well known in the art and include, by way of example and not limitation, polyesters such as polyglycolides, polylactides and polylactic polyglycolic acid copolymers (PLGA) (Langer and Folkman, Nature 263:797-800, 1976); hydrogels (e.g., cross-linked gelatin, poly(ethylene glycol monomethacrylate); polyethylene glycols (PEG) and their derivatives, including, but not limited to, cetomacrogol, hydrogel, nonoxynol, octoxynol, poloxalene, poloxamer, polyhydroxyethyl methacrylate, and polysorbates; polyaminotrizoles; polyethers such as polycaprolactone (PCL); polyanhydrides; polyalkyl cyanoacrylates such as n-butyl cyanoacrylate and isopropyl cyanoacrylate; polyacrylamides; poly(orthoesters); polyphosphazenes; polypeptides; polyurethanes; and mixtures of such polymers. Preferred polyanhydrides of the invention include, for example, the family of photopolymerizable, methacrylated anhydride monomers and oligomers described in Anseth et al., *Nature Biotech.* 17:156-159, 1999, incorporated by reference. These anhydides react to form cross-linked degradable biocompatible networks suitable as matrices.

It should be understood that virtually any polymer that is known or that will be later developed that is suitable for the sustained or controlled release of nucleic acids and can be formed into a shape that allows cellular ingrowth may be employed in the present invention.

Four polymers that have been widely used in medical applications are poly(paradioxanone) (PDS), poly(lactic acid) (PLA), poly(glycolic acid) (PGA), and polylactic polyglycolic acid copolymers (PLGA). Copolymerization enables modulation of the degradation time of the material. By changing the ratios of crystalline to amorphous polymers during polymerization, properties of the resulting material can be altered to suit the needs of the application. These polymers, including poly(lactide-co-glycolic) acid (PLGA), have been used as polymer composites for bone replacement as reported by Elgendy et al., *Biomaterials* 14:263-269, 1993. Substituted polyphosphazenes have been shown to support osteogenic cell ingrowth, as reported by Laurencin et al., *J. Biom. Mater. Res.* 27, 1993. Poly(organophosphazenes) are high molecular weight polymers containing a backbone of alternating phosphorus and nitrogen atoms. There are a wide variety of polyphosphazenes, each derived from the same precursor polymer, poly(dichlorophosphazene). The chlorine-substituted species can be modified by replacement of the chlorine atoms by different organic nucleophiles such as o-methylphenoxide along with amino acids. The physical and chemical properties of the polymer can be altered by adding various ratios of hydrolytic sensitive side chains such as ethyl glycinate, as described by Wade et al., in Organomet. Polym., Carraher, Sheats and Pitman, Jr., Eds., Academic Press, New York, pp. 283-288, 1978; and Allcock and Fuller, *J. Am. Chem. Soc.* 103:2250-2256, 1981. This will affect the degradation of the polymer as an implantable and biodegradable material as well as vary the support of osteogenic cells for bone and tissue implants.

PLA, PGA and PLGA copolymers are particularly useful for forming the biodegradable matrices of the present invention. PLA polymers are usually prepared from the cyclic esters of lactic acids. Both L(+) and D(−) forms of lactic acid can be used to prepare the PLA polymers, as well as the optically inactive DL-lactic acid mixture of D(−) and L(+) lactic acids. Methods of preparing polylactides are well known in the art. PGA is the homopolymer of glycolic acid (hydroxyacetic acid). In the conversion of glycolic acid to poly(glycolic acid), glycolic acid is initially reacted with itself to form the cyclic ester glycolide, which in the presence of heat and a catalyst is converted to a high molecular weight linear-chain polymer.

The erosion of the matrix is related to the molecular weights of PLA, PGA or PLGA. The higher molecular weights, weight average molecular weights of 90,000 or higher, result in polymer matrices which retain their structural integrity for longer periods of time; while lower molecular weights, weight average molecular weights of 30,000 or less, result in both slower release and shorter matrix lives. Poly(lactide-co-glycolide) (50:50), degrades in about six weeks following implantation.

All polymers for use in the matrix must meet the mechanical and biochemical parameters necessary to provide adequate support for the cells with subsequent growth and proliferation. The polymers can be characterized with respect to mechanical properties such as tensile strength using an Instron tester, for polymer molecular weight by gel permeation chromatography (GPC), glass transition temperature by differential scanning calorimetry (DSC) and bond structure by infrared (IR) spectroscopy, with respect to toxicology by initial screening tests involving Ames assays and in vitro teratogenicity assays, and implantation studies in animals for immunogenicity, inflammation, release and degradation studies.

These polymers are particularly useful in forming fibrous or sponge type matrices for implantation. In preferred embodiments, the biocompatible biodegradable polymer is a copolymer of glycolic acid and lactic acid (PLGA) having a proportion between the lactic acid/glycolic acid units ranging from about 100/0 to about 25/75. The average molecular weight ("MW") of the polymer will typically range from about 6,000 to 700,000 and preferably from about 30,000 to 120,000, as determined by gel-permeation chromatography using commercially available polystyrene of standard molecular weight, and have an intrinsic viscosity ranging from 0.5 to 10.5.

As noted above, the length of the period of continuous sustained or controlled release of nucleic acids from the matrix according to the invention will depend in large part on the MW of the polymer and the composition ratio of lactic acid/glycolic acid. Generally, a higher ratio of lactic acid/glycolic acid, such as for example 75/25, will provide for a longer period of controlled of sustained release of the nucleic acids, whereas a lower ratio of lactic acid/glycolic acid will provide for more rapid release of the nucleic acids. Preferably, the lactic acid/glycolic acid ratio is 50/50.

The length of period of sustained or controlled release is also dependent on the MW of the polymer. Generally, a higher MW or higher crosslinked polymer will provide for a longer period of controlled or sustained release. In the case of preparing, for example, matrices providing controlled or sustained release for about three months, when the composition ratio of lactic acid/glycolic acid is 100/0, the preferable average MW of polymer ranges from about 7,000 to 25,000; when 90/10, from about 6,000 to 30,000; and when 80/20, from about 12,000 to 30,000.

Another particular example of a suitable material is fibrous collagen, which may be lyophilized following extraction and partial purification from tissue and then, sterilized. Matrices may also be prepared from tendon or dermal collagen, as may be obtained from a variety of commercial sources, such as, e.g., Sigma and Collagen Corporation. Collagen matrices may also be prepared as described in U.S. Pat. Nos. 4,394,370 and 4,975,527, each incorporated herein by reference.

In addition, lattices made of collagen and glycosaminoglycan (GAG) such as that described in Yannas & Burke, U.S. Pat. No. 4,505,266, may be used in the practice of the invention. The collagen/GAG matrix may effectively serve as a support or "scaffolding" structure into which cells may migrate. Collagen matrices, such as those disclosed in Bell, U.S. Pat. No. 4,485,097, may also be used as a matrix material.

The various collagenous materials may also be in the form of mineralized collagen. For example, the fibrous collagen implant material termed UltraFiber™, as may be obtained from Norian Corp., (Mountain View, Calif.) may be used for formation of matrices. U.S. Pat. No. 5,231,169, incorporated herein by reference, describes the preparation of mineralized collagen through the formation of calcium phosphate mineral under mild agitation in situ in the presence of dispersed collagen fibrils. Such a formulation may be employed in the context of delivering a nucleic acid molecule to a tissue site. Mineralized collagen, as with any matrix composition, may be employed, for example, as part of kit for producing an in situ bioreactor for use in vivo.

A variety of different forms of collagen have been identified and each of these collagens may be used in the practice of the invention. For example, collagen may be purified from hyaline cartilage, as isolated from diarthrodial joints or growth plates. Type II collagen purified from hyaline cartilage is commercially available and may be purchased from, e.g., Sigma Chemical Company, St. Louis. Type I collagen from bovine hides may be purchased from, e.g., Collagen Corporation. Any form of recombinant collagen may also be employed, as may be obtained from a collagen-expressing recombinant host cell, including bacterial yeast, mammalian, and insect cells. When using collagen as a matrix material it may be advantageous to remove what is referred to as the "telopeptide" which is located at the end of the collagen molecule. The resulting atelocollagen is known to decrease the inflammatory response toward collagen.

The collagen used in the invention may, if desired be supplemented with additional minerals, such as calcium, e.g., in the form of calcium phosphate. Admixing, absorbing, or otherwise associating with additional minerals in this manner may supplement both native and recombinant type collagen.

In one embodiment the matrix comprises a hydrogel. The term "hydrogel", as used herein, refers to a three dimensional network of cross-linked hydrophilic polymers. The network is in the form of a gel substantially composed of water, preferably but not limited to gels being greater than 90% water. Cross-linked hydrogels can also be considered solids because they do not flow or deform without appreciable applied shear stress. Compositions that form hydrogels generally fall into three classes. The first class carries a net negative charge and is typified by alginate. The second class carries a net positive charge and is typified by extracellular matrix components such as collagen and laminin. Examples of commercially available extracellular matrix components include MATRIGEL™ and VITROGEN™. The third class is net neutral in charge. An example of a net neutral hydrogel is highly crosslinked polyethylene oxide, or polyvinylalcohol.

Polymers that can form ionic hydrogels that are malleable can also be used to support the cells. Injecting a suspension of nucleic acid molecules, a gene delivery device, or cells into a polymer solution may be performed to improve the reproducibility and uniformity throughout a matrix, to protect the components from shear forces or pressure induced necrosis (for cells), or to aid in defining the spatial location. The injectable polymer may also be utilized to deliver bi-gene devices or in situ bioreactors and promote the formation of new tissue without the use of any other matrix. In a preferred embodiment, the hydrogel is produced by cross-linking the ionic salt of a polymer with ions. The strength of the hydrogel increases with either increasing concentrations of ions or polymer. The polymer solution is mixed with the appropriate components, such as nucleic acid molecules, gene delivery compositions, polypeptides, etc. to form a suspension, which is then injected directly into a patient prior to hardening of the suspension. The suspension subsequently hardens over a short period of time due to the presence in vivo of physiological concentrations of ions such as calcium, as is the case where the polymer is a polysaccharide such as alginate.

A "hydrogel", as used herein is a matrix composition, and is a substance formed when an organic polymer (natural or synthetic) is cross-linked via covalent, ionic, or hydrogen bonds to create a three-dimensional open-lattice structure which entraps water molecules to form a gel. Examples of materials which can be used to form such a hydrogel include polysaccharides such as alginate, polyphosphazenes, and polyacrylates such as hydroxyethyl methacrylate (HEMA), which are crosslinked ionically, or block copolymers such as PLURONICS™ or TETRONICS™, polyethylene oxide-polypropylene glycol block copolymers which are crosslinked by temperature or pH, respectively. Other materials include proteins such as fibrin, polymers such as polyvinylpyrrolidone, hyaluronic acid and collagen.

In general, these polymers are at least partially soluble in aqueous solutions, such as water, buffered salt solutions, or aqueous alcohol solutions, that have charged side groups, or a monovalent ionic salt thereof. Examples of polymers with acidic side groups that can be reacted with cations are poly(phosphazenes), poly(acrylic acids), poly(methacrylic acids), copolymers of acrylic acid and methacrylic acid, poly(vinyl acetate), and sulfonated polymers, such as sulfonated polystyrene. Copolymers having acidic side groups formed by reaction of acrylic or methacrylic acid and vinyl ether monomers or polymers can also be used. Examples of acidic groups are carboxylic acid groups, sulfonic acid groups, halogenated (preferably fluorinated) alcohol groups, phenolic OH groups, and acidic OH groups. Examples of polymers with basic side groups that can be reacted with anions are poly(vinyl amines), poly(vinyl pyridine), poly(vinyl imidazole), and some imino substituted polyphosphazenes. The ammonium or quaternary salt of the polymers can also be formed from the backbone nitrogens or pendant imino groups. Examples of basic side groups are amino and imino groups.

Alginate can be ionically cross-linked with divalent cations, in water, at room temperature, to form a hydrogel matrix. Due to these mild conditions, alginate has been the most commonly used polymer for cell encapsulation, as described, for example, in U.S. Pat. No. 4,352,883 to Lim. In the Lim process, an aqueous solution containing the biological materials to be encapsulated is suspended in a solution of a water soluble polymer, the suspension is formed into droplets which are configured into discrete microcapsules by contact with multivalent cations, then the surface of the microcapsules is crosslinked with polyamino acids to form a semipermeable membrane around the encapsulated materials.

The polyphosphazenes suitable for cross-linking have a majority of side chain groups which are acidic and capable of forming salt bridges with di- or trivalent cations. Examples of preferred acidic side groups are carboxylic acid groups and sulfonic acid groups. Hydrolyrically stable polyphosphazenes are formed of monomers having carboxylic acid side groups that are crosslinked by divalent or trivalent cations such as $Ca^{2+}$ or $Al^{3+}$. Hydrogel forming polymers may be synthesized to degrade by hydrolysis by incorporating monomers having imidazole, amino acid ester, or glycerol side groups. Biodegradable polyphosphazenes have at least two differing types of side chains, acidic side groups capable of forming salt bridges with multivalent cations, and side groups that hydrolyze under in vivo conditions, e.g., imidazole groups, amino acid esters, glycerol and glucosyl.

The water soluble polymer with charged side groups is crosslinked by reacting the polymer with an aqueous solution containing multivalent ions of the opposite charge, either multivalent cations if the polymer has acidic side groups or multivalent anions if the polymer has basic side groups. The preferred cations for cross-linking of the polymers with acidic side groups to form a hydrogel are divalent and trivalent cations such as copper, calcium, aluminum, magnesium, strontium, barium, and tin, although di-, tri- or tetra-functional organic cations such as alkylammonium salts, can also be used. Aqueous solutions of the salts of these cations are added to the polymers to form soft, highly swollen hydrogels and membranes. The higher the concentration of cation, or the higher the valence, the greater the degree of cross-linking of the polymer. Concentrations from as low as 0.005 M have been demonstrated to cross-link the polymer, Higher concentrations are limited by the solubility of the salt. The preferred anions for cross-linking of the polymers to form a hydrogel are divalent and trivalent anions such as low molecular weight dicarboxylic acids, for example, terepthalic acid, sulfate ions and carbonate ions. Aqueous solutions of the salts of these anions are added to the polymers to form soft, highly swollen hydrogels and membranes, as described with respect to cations.

A variety of polycations can be used to complex and thereby stabilize the polymer hydrogel into a lattice. Examples of materials that can be used include polymers having basic reactive groups such as amine or amine groups, having a preferred molecular weight between 3,000 and 100,000, such as polyethylenimine and polylysine. These are commercially available. One polycation is poly(L-lysine), examples of synthetic polyamines are: polyethyleneimine, poly(vinylamine), and poly(allyl amine). There are also natural polycations such as the polysaccharide, chitosan. Polyanions that can be used by reaction with basic surface groups on the polymer hydrogel include polymers and copolymers of acrylic acid, methacrylic acid, and other derivatives of acrylic acid, polymers with pendant $SO_3H$ groups such as sulfonated polystyrene, and polystyrene with carboxylic acid groups.

Accordingly, virtually any gel can be used in the practice of the present invention. The materials which can be used to form such gels include but are not limited to: carbohydrates such as cellulosics, methylcellulose, starch and modified starch, agarose, gum arabic, ghatti, karay, tragacanth, guar, locust bean gum, tamarind, carageenan, alginate, xanthan, chickle, collagen, polyacrylamide, polyethylene glycols (PEG) and their derivatives (including but not limited to cetomacrogol, hydrogel, nonoxynol, octoxynol, poloxalene, poloxamer, polyhydroxyethyl methacrylate, and polysorbates); polysiloxanes (polyanhydrides, e.g., malic anhydride copolymers, polyacrylates, e.g., hydroxyethylpolymethycrylate, polymethylmethacrylate, polyethylethacrylate, polymethacrylate, poloxamers (Pluronics), ethylenevinylacetate copolymers, ethylenevinylalcohol copolymers, polyorthoesters, ε-caprolactones, amino acid polymers such as gelled albumin, amino acid polymers and copolymers and gelatins, and other organic or inorganic polymers which may be mixed with liposomes in vitro.

In certain embodiments, the gene-activated matrix should have sufficient surface area and exposure to nutrients such that cellular ingrowth and differentiation can occur prior to or concurrent to the ingrowth of blood vessels. After implantation, the configuration should allow for diffusion of nutrients and waste products and for continued blood vessel ingrowth as cell proliferation occurs. The organization of the growing tissue may be regulated by the microstructure of the matrix. Specific pore sizes and structures may be utilized to control the pattern and extent of fibrovascular tissue ingrowth from the host. Accordingly, if cells are seeded in the matrix before implantation the organization of the seeded cells may also be guided. The surface geometry and chemistry of the matrix may be regulated to control the adhesion (e.g., by extracellular matrix proteins such as laminin, collagen, thrombospondin, collagen, elastin, fibronectin, tenascin, entactin, vitronectin, and the like), organization, and function of seeded cells or in growing host cells.

In certain embodiments, the matrix is formed of polymers having a fibrous structure which has sufficient interstitial spacing typically in the range of 100 to 300 microns (see, Friedlander and Goldberg, Bone and Cartilage Allografts, Park Ridge: American Academy of Orthopedic Surgeons, 1991; Jarcho, Clin. Orth. Rel. Res. 157:259-278, 1981. As used herein, "fibrous" includes one or more fibers that is entwined with itself, multiple fibers in a woven or non-woven mesh, and sponge like devices.

In certain various embodiments of the invention, the matrix may comprise or be modified, e.g., coated or impregnated, prior to implantation with certain substances to enhance the attachment and growth of cells on the matrix in vivo. These substances include, but are not limited to, bioactive agents such cellular growth factors (e.g., TGF-β, FGF, etc.), substances that stimulate chondrogenesis (e.g., BMPs that stimulate cartilage formation such as BMP-2, BMP-12 and BMP-13), factors that stimulate migration of cells to the matrix, factors that stimulate matrix deposition, anti-inflammatories (e.g., non-steroidal anti-inflammatories), immunosuppressants (e.g., cyclosporins), as well as other proteins, such as collagens, elastic fibers, reticular fibers, glycoproteins or glycosaminoglycans, such as heparin sulfate, chondroitin-4-sulfate, chondroitin-6-sulfate, dermatan sulfate, keratin sulfate, etc. For example, growth factors such as TGF-β, with ascorbate, have been found to trigger cell differentiation and cartilage formation by chondrocytes. The bioactive agent may also be a cell retention agent, such as laminin, fibronectin or the like to adhere cells to the matrix, or may be an active inhibitor of cellular migration such as macrophage migration inhibitory factor (MIF). One of ordinary skill in the art will readily recognize that such agents may either be in the form of polypeptides or in the form of nucleic acid molecules encoding such polypeptides, such that upon implantation such nucleic acid molecules are taken up by the migrating cells and expressed.

Nucleic Acid Molecules

The present methods and compositions may employ a variety of different types of nucleic acid molecules. Accordingly, the nucleic acid molecules may include genomic, cDNAs, single stranded DNA, double stranded DNA, triple stranded DNA, oligonucleotides and Z-DNA. The RNA molecules may include messenger RNA, sense RNA, and antisense RNA.

The DNA molecules may code for a variety of therapeutic agents that promote tissue repair, angiogenesis or regeneration, including extracellular, cell surface, and intracellular proteins and RNAs. Examples of extracellular proteins include growth factors, cytokines, extracellular matrix molecules, therapeutic proteins, hormones and peptide fragments of hormones, inhibitors of cytokines, peptide growth and differentiation factors, interleukins, chemokines, interferons, colony stimulating factors and angiogenic factors. Examples of such proteins include, but are not limited to, the superfamily of TGF-β molecules, including the TGF-β isoforms and bone morphogenetic proteins (BMP) such as BMP2, BMP3, BMP4, BMP5, BMP6, BMP7, BMP8, BMP9, BMP10, BMP11, BMP12, or BMP13; cartilage-derived morphogenic protein (CDMP); latent TGF-β binding proteins (LTBP); keratinocyte growth factor (KGF); hepatocyte growth factor (HGF); platelet derived growth factor (PDGF); insulin-like growth factor (IGF); the fibroblast growth factors (FGF-1, FGF-2, etc.), epidermal growth factors (EGFs); connective tissue growth factor (CTGF); skeletal growth factor (SGF); vascular endothelial growth factor (VEGF); leukemia inhibitory factor (LIF); parathyroid hormone-related peptide (PTHrP); activins; inhibins; interleukins (IL); macrophage-colony stimulating factor (M-CSF); and granulocyte macrophage-colony stimulating factor (GM-CSF). In specific embodiments, the polypeptide growth factor is, for example, PDGF-AA, PDGF-BB, PDGF-AB, HGF, FGF-1, FGF-2, FGF-3, FGF-4, FGF-5, FGF-6, FGF-7, FGF-8, FGF-9, FGF-10, FGF-11, FGF-12, FGF-13, FGF-14, FGF-15, FGF-16, FGF-17, FGF-18, FGF-19, FGF-20, FGF-21, TGF-α, TGF-β1, TGF-β2, or TGF-β3. In a further embodiment, the DNA may encode for a zinc-finger binding protein, cell survival factors (e.g. BCL-2), transcription factors, or mono or polyclonal antibodies or soluble receptors that bind to mediators of inflammation. Hormones that may be used in the practice of the invention include, for example, growth hormone (GH) and parathyroid hormone (PTH). Examples of extracellular proteins also include the extracellular matrix proteins such as collagen, laminin, and fibronectin. Examples of cell surface proteins include the family of cell adhesion molecules (e.g., the integrins, selectins, Ig family members such as N-CAM and L1, and cadherins); cytokine signaling receptors such as the TGF receptors and the FGF receptor; and non-signaling co-receptors such as betaglycan and syndecan. Examples of intracellular RNAs and proteins include the family of signal transducing kinases, cytoskeletal proteins such as talin and vinculin, cytokine binding proteins such as the family of latent TGF-β binding proteins, and nuclear trans-acting proteins such as transcription factors, chromatin-associated proteins, and proteins which regulate mRNA stability and turnover.

The DNA molecules may also code for proteins that block pathological processes, thereby allowing the natural wound healing process to occur unimpeded. Examples of blocking factors include ribozymes that destroy RNA function and DNAs that, for example, code for tissue inhibitors of enzymes that destroy tissue integrity, e.g., inhibitors of metalloproteinases associated with arthritis.

One may obtain the DNA segment encoding the protein of interest using a variety of molecular biological techniques, generally known to those skilled in the art. For example, cDNA or genomic libraries may be screened using primers or probes with sequences based on the known nucleotide sequences. Polymerase chain reaction (PCR) may also be used to generate the DNA fragment encoding the protein of interest. Alternatively, the DNA fragment may be obtained from a commercial source. Nucleic acid sequences of interest are available in the art and from Genbank databases.

The nucleic acid molecules useful in the present invention include those possessing naturally occurring nucleotide sequences and functional variants thereof. Polypeptides can be encoded by nucleic acids that, by virtue of the degeneracy of the genetic code, are not identical in sequence to naturally occurring genes, cDNAs, or mRNAs. Variants and mutants can include amino acid substitutions, additions or deletions. Amino acid substitutions can be conservative amino acid substitutions or substitutions to eliminate non-essential amino acids, such as to alter a glycosylation site, a phosphorylation site or an acetylation site, or to minimize misfolding by substitution or deletion of one or more cysteine residues. Conservative amino acid substitutions are those that preserve the general characteristics of the polypeptide, including charge, hydrophobicity/hydrophilicity, and/or steric bulk of the amino acid substituted.

Techniques for introducing changes in nucleotide sequences that are designed to alter the functional properties of the encoded proteins or polypeptides are well known in the art. Such modifications include the deletion, insertion or substitution of bases that result in changes in the amino acid sequence. Changes may be made to increase the activity of an encoded protein, to increase its biological stability or half-life, to change its glycosylation pattern, confer temperature sensitivity or to alter the expression pattern of the protein and the like. All such modifications to the nucleotide sequences are encompassed by this invention.

The DNA encoding the translational or transcriptional products of interest may be recombinantly engineered into a variety of vector systems that provide for the replication of the DNA in large scale to prepare the nucleic acid-activated matrices. These vectors can be designed to contain the necessary elements for directing the transcription and/or translation of the DNA sequence taken up by the repair cells at the wound in vivo.

Any number of vectors is within the scope of the present invention. Vectors that may be used include, but are not limited to those derived from recombinant bacteriophage DNA, plasmid DNA or cosmid DNA. For example, plasmid vectors such as pBR322, pUC 19/18, pUC 118, 119 and the M13 mp series of vectors may be used. Bacteriophage vectors may include λgt10, λgt11, λgt18-23, λZAP/R and the EMBL series of bacteriophage vectors. Vectors derived from other double-stranded DNA bacteriophage, for example T1, T2, T4, T6, T3, T7, and T5, may also be utilized in the present invention.

Vectors using filamentous phage, so-called phagemids, combining features of plasmids and phages, may also be utilized in the present invention. Filamentous phage encompasses a group of bacteriophages that are able to infect a variety of Gram-negative bacteria through interaction with the tip of the F pilus. Well known filamentous phages include M13, f1, and fd. The genomes of these phage are single-stranded DNA, but replicate through a double-stranded form. Phage particles are assembled in the bacteria and extruded into the media. Because the bacteria continue to grow and divide, albeit at a slower rate than uninfected cells, relatively high titers of phage are obtained. Moreover, replication and assembly appear to be unaffected by the size of the genome. As a consequence of their structure and life cycle, the filamentous phage have become a valuable addition in the arsenal of molecular biology tools.

Cosmid vectors that may be utilized include, but are not limited to, pJB8, pCV 103, pCV 107, pCV 108, pTM, pMCS, pNNL, pHSG274, COS202, COS203, pWE15, pWE16 and the charomid 9 series of vectors.

Vectors that allow for the in vitro transcription of RNA, such as SP6 vectors, may also be used to produce large quantities of RNA that may be incorporated into matrices. Alternatively, recombinant virus vectors including, but not limited to those derived from viruses such as herpes virus, retroviruses, vaccinia viruses, adenoviruses, adeno-associated viruses or bovine papilloma virus may be engineered. While integrating vectors may be used, non-integrating systems, which do not transmit the gene product to daughter cells for many generations are preferred for wound healing. In this way, the gene product is expressed during the wound healing process, and as the gene is diluted out in progeny generations, the amount of expressed gene product is diminished.

Methods which are well known to those skilled in the art can be used to construct expression vectors containing the protein coding sequence operatively associated with appropriate transcriptional/translational control signals. These methods include in vitro recombinant DNA techniques, and synthetic techniques. See, for example, the techniques described in Sambrook, et al., 1992, Molecular Cloning, A Laboratory Manual, Cold Spring Harbor Laboratory, N.Y. and Ausubel et al., 1989, Current Protocols in Molecular Biology, Greene Publishing Associates & Wiley Interscience, N.Y.

The genes encoding the proteins of interest may be operatively associated with a variety of different promoter/einhancer elements. The expression elements of these vectors may vary in their strength and specificities. Depending on the host/vector system utilized, any one of a number of suitable transcription and translation elements may be used. The promoter may be in the form of the promoter which is naturally associated with the gene of interest. Alternatively, the DNA may be positioned under the control of a recombinant or heterologous promoter, i.e., a promoter that is not normally associated with that gene. For example, tissue specific promoter/enhancer elements may be used to regulate the expression of the transferred DNA in specific cell types. Examples of transcriptional control regions that exhibit tissue specificity which have been described and could be used include, but are not limited to: elastase I gene control region which is active in pancreatic acinar cells (Swift et al., Cell 38:639-646, 1984; Ornitz et al., *Cold Spring Harbor Symp. Quant. Biol.* 50:399-409, 1986; MacDonald, *Hepatology* 7:42S-51S, 1987); insulin gene control region which is active in pancreatic beta cells (Hanahan, *Nature* 315:115-122, 1985); immunoglobulin gene control region which is active in lymphoid cells (Grosschedl et al., Cell 38:647-658, 1984; Adams et al., *Nature* 318:533-538, 1985; Alexander et al., *Mol. Cell. Biol.* 7:1436-1444, 1987): albumin gene control region which is active in liver (Pinkert et al., *Genes and Devel.* 1:268-276, 1987) alpha-fetoprotein gene control region which is active in liver (Krumlauf et al., *Mol. Cell. Biol.* 5:1639-1648, 1985; Hammer et al., *Science* 235:53-58, 1987); alpha-1-antitrypsin gene control region which is active in liver (Kelsey et al., *Genes and Devel.* 1:161-171, 1987); beta-globin gene control region which is active in myeloid cells (Magram et al., *Nature* 315:338-340, 1985; Kollias et al., *Cell* 46:89-94, 1986); myelin basic protein gene control region which is active in oligodendrocyte cells in the brain (Readhead et al., *Cell* 48:703-712, 1987); myosin light chain-2 gene control region which is active in skeletal muscle (Shani, *Nature* 314:283-286, 1985); and gonadotropic releasing hormone gene control region which is active in the hypothalamus (Mason et al., *Science* 234:1372-1378, 1986). Promoters isolated from the genome of viruses that grow in mammalian cells, (e.g., RSV, vaccinia virus 7.5K, SV40, HSV, adenoviruses MLP, MMTV LTR and CMV promoters) may be used, as well as promoters produced by recombinant DNA or synthetic techniques. It is understood that cells comprising the target tissue associated with the fluid space may take up and express the therapeutic DNA. It may, therefore, be advantageous to use DNA vectors containing target tissue specific promoter/enhancer elements, and it is within the scope of the current invention to utilize such elements according to claimed methods and within claimed compositions. Thus, in certain embodiments, vectors will be constructed to maximize expression in infiltrating repair cells, so as to provide a universal vector for use in targeting a wide range of tissues. In other embodiments, vectors may be constructed to maximize expression within target tissue cells. One preferred embodiment utilizes vectors capable of high level expression in both infiltrating repair cells and target tissue cells.

In some instances, the promoter elements may be constitutive or inducible promoters and can be used under the appropriate conditions to direct high level or regulated expression of the gene of interest. Expression of genes under the control of constitutive promoters does not require the presence of a specific substrate to induce gene expression and will occur under all conditions of cell growth. In contrast, expression of genes controlled by inducible promoters is responsive to the presence or absence of an inducing agent.

Specific initiation signals are also required for sufficient translation of inserted protein coding sequences. These signals include the ATG initiation codon and adjacent sequences. In cases where the entire coding sequence, including the initiation codon and adjacent sequences are inserted into the appropriate expression vectors, no additional translational control signals may be needed. However, in cases where only a portion of the coding sequence is inserted, exogenous translational control signals, including the ATG initiation codon must be provided. Furthermore, the initiation codon must be in phase with the reading frame of the protein coding sequences to ensure translation of the entire insert. These exogenous translational control signals and initiation codons can be of a variety of origins, both natural and synthetic. The efficiency and control of expression may be enhanced by the inclusion of transcription attenuation sequences, enhancer elements, etc.

Nucleic acids may be propogated and produced in a substantially pure form suitable for therapeutic use by any means available in the art. Nucleic acids may be cloned into a variety of vector systems that provide for replication and production of large amounts of DNA in host cells, including plasmids, viruses, episomes, cosmids and bacteriophage. Vectors are transferred to host cells by known methods including transfection, transformation or infection. Suitable host cells may include bacteria such as *E. coli*, yeast, plant cells, mammalian tissue culture cells or baculovirus. Techniques for propagating and purifying recombinant nucleic acid vectors are well known in the art and are described in Sambrook et al. 1992 Molecular Cloning, A Laboratory Manual, Cold Spring Harbor Laboratory, N.Y. and Ausubel et al., 1989 Current Protocols in Molecular Biology, Greene Publishing Associates and Wiley Interscience, N.Y. Alternatively, nucleic acid molecules may be chemically synthesized.

It is within the scope of the invention that multiple genes, combined on a single genetic construct under control of one or more promoters, or prepared as separate constructs of the same or different types may be used. Thus, an almost endless combination of different genes and genetic constructs may be employed. Certain gene combinations may be designed to, or their use may otherwise result in, achieving synergistic effects on cell stimulation and regeneration, any and all such combinations are intended to fall within the scope of the present invention. Indeed, many synergistic effects have been described in the scientific literature, so that one of ordinary skill in the art would readily be able to identify likely synergistic gene combinations, or even gene-protein combinations.

It is also within the scope of the invention that nucleic acids used in the invention include those encoding recombinant fusion protein. Fusion proteins may consist of two or more polypeptides or fragments thereof. In certain embodiments, fusion proteins comprise a therapeutic polypeptide tagged with an immunogenic epitope such as the FLAG epitope (Kodak) which can be used to examine expression and delivery of the therapeutic protein by immunological methods known in the art such as ELISA, western blot or radioimmunoassay (RIA). In specific embodiments, fusion proteins contain a targeting moiety introduced to promote efficient uptake of a fused therapeutic polypeptide into target cells. Examples of targeting moieties include immunoglobulins and ligands which bind target cell surface receptors.

It is also within the scope of the invention that nucleic acids used in the invention are complexed with anti-DNA antibodies prior to their in vivo delivery. Anti-DNA antibodies are commercially available from, for example, Sigma (Sigma-Aldrich Corporation, St. Louis, Mo.) and USB (USB Corporation, Cleveland, Ohio). Illustrative anti-DNA antibodies include, but are not limited to, mouse anti-DNA (IgM, IgG2b) and human anti-double stranded (ds)DNA from lupus patient sera. Plasmids may first be incubated with anti-DNA antibodies, during which time the antibodies bind to the plasmids. The antibody-plasmid complexes may then be formulated in the desired delivery vehicle. Formulation can occur in relatively simple buffers such as buffered saline, or, if desired, in biocompatible matrices such as those described herein to form GAMs. In a related embodiment, histone H1 and protamine may also be used to form DNA complexes for use in the GAMs of the present invention. The materials are then ready for in vivo delivery.

Without being bound by theory, several desirable effects may be achieved by using antibody-plasmid complexes as compared to plasmids alone. The bound antibodies may restrict degradative enzymes, such as DNases, from binding to the plasmids. This would inhibit plasmid degradation, and thus enhance plasmid stability. Another effect is that cellular uptake may be improved. For example, cells with immunoglobulin receptors, such as Fc receptors, may now bind and internalize the antibody-plasmid complexes. Antibody-plasmid complexes may also allow for improved cellular uptake through non-receptor mediated processes, such as pinocytosis. Some of these processes would be analogous to opsonization. Once internalized, intracellular trafficking and nuclear delivery of antibody-plasmid complexes may also be superior to free or "naked" plasmids, and as a result the chance of a productive transgene expression would be improved. An additional positive effect is that, in the case of GAMs, plasmid association with the biocompatible matrix may be improved. This would lead to an improved retention and prolonged activity of plasmids at delivery sites.

One result of antibody-plasmid binding may be the formation of discrete particles. This would be analogous to the formation of "plasmid condensates" through the use of agents such as polylysine. Condensation into particles is generally a positive event, as particles often physically limit access of degradative enzymes to plasmids, and as cells often more effectively internalize complexes as compared to free plasmids. However, it should be noted that the formation of particles is not specifically a prerequisite for using anti-DNA antibody-plasmid formulations, as these beneficial events may also occur when antibodies simply coat plasmids, but do not form larger cross-linked structures.

In addition to DNA sequences encoding therapeutic proteins of interest, the scope of the present invention includes the use of ribozymes or antisense DNA molecules that may be transferred into the mammalian repair cells. Such ribozymes and antisense molecules may be used to inhibit the translation of RNA encoding proteins of genes that inhibit a disease process or the wound healing process thereby allowing tissue repair to take place.

Antisense nucleic acids are designed to specifically bind to RNA, resulting in the formation of RNA-DNA or RNA-RNA hybrids and an arrest in DNA replication, reverse transcription or messenger RNA translation. Antisense polynucleotides based on a selected sequence can specifically interfere with expression of the corresponding gene. Antisense polynucleotides are typically generated within the cell by expression from antisense constructs that contain the antisense strand as the transcribed strand. Antisense production and uses thereof are discussed extensively in the literature and are widely known and available to one skilled in the art.

Ribozymes are trans-cleaving catalytic RNA molecules possessing endoribonuclease activity. Ribozymes are specifically designed for a particular target nucleotide sequence. Ribozymes are engineered to cleave an RNA species site-specifically in the background of cellular RNA. The cleavage event renders the mRNA unstable and prevents protein expression. Preparation and usage of ribozymes is well known to the art (see Usman et al., *Current Opin. Struct. Biol.* 6:527-533, 1996; Long et al., *FASFB J.* 7:25, 1993; Symons, *Ann. Rev. Biochem.* 61:641, 1992 and U.S. Pat. No. 5,254, 678). Knowledge of the nucleotide sequence of the target ribonucleic acid molecule allows construction of an effective ribozyme.

RNAs utilized in the invention may be produced by any means known in the art, such as in vitro synthesis from a vector directing transcription from a promoter such as T3, T7 or Sp6, as described in Ausubel et al., 1989, Current Protocols in Molecular Biology, Greene Publishing Associates and Wiley Interscience, N.Y.

In certain embodiments, nucleic acid molecules encoding the therapeutic agent may be utilized in gene delivery vehicles. Any method of gene delivery available in the art may be utilized according to the present invention. Gene delivery vehicle may be of viral or non-viral origin (see generally, Jolly, *Cancer Gene Therapy* 1:51-64, 1994; Kimura, *Human Gene Therapy* 5:845-852, 1994; Connelly, *Human Gene Therapy* 1:185-193, 1995; and Kaplitt, *Nature Genetics* 6:148-153, 1994). Expression of coding sequences can be controlled using endogenous mammalian or heterologous promoters and may be either constitutive or regulated. Nucleic acids used according to the invention may be stably integrated into the genome of the cell or may be maintained in the cell as separate episomal segments of DNA.

The present invention can employ recombinant retroviruses that are constructed to carry or express a selected nucleic acid molecule of interest. Methods of producing recombinant retroviral virions suitable for gene therapy have been extensively described (see,-e.g., Mann et al., *Cell* 33:153-159, 1983, and Nikolas and Rubenstein, Vectors: A survey of molecular cloning vectors and their uses, Rodriquez and Denhardt (eds.), Stoneham: Butterworth, 494-513, 1988).

The present invention also employs viruses such as alphavirus-based vectors, adenovirus and parvovirus that can function as gene delivery vehicles. In certain embodiments of the invention, adenovirus or adenovirus-derived vectors are utilized for introduction of one or more nucleic acid molecules. Examples of vectors utilized by the invention include intact adenovirus, replication-defective adenovirus vectors requiring a helper plasmid or virus, and adenovirus vectors with their native tropism modified or ablated including adenoviral vectors containing a targeting ligand. In specific embodiments, the targeting ligand is a polypeptide reactive with a cell surface receptor such as an FGF receptor. Vector compositions, systems and methods for using these adenovirus vectors are disclosed in WO 98/40508 that is incorporated by reference in its entirety. Various adeno-associated virus (AAV) vector systems have also been developed for polynucleotide delivery. AAV vectors can be readily constructed using techniques well known in the art. See, e.g., U.S. Pat. Nos. 5,173,414 and 5,139,941; International Publication Nos. WO 92/01070 and WO 93/03769; Lebkowski et al. (1988) *Molec. Cell. Biol.* 8:3988-3996; Vincent et al. (1990) Vaccines 90 (Cold Spring Harbor Laboratory Press); Carter, B. J. (1992) *Current Opinion in Biotechnology* 3:533-539; Muzyczka, N. (1992) *Current Topics in Microbiol. and Immunol.* 158:97-129; Kotin, R. M. (1994) *Human Gene Therapy* 5:793-801; Shelling and Smith (1994) *Gene Therapy* 1:165-169; and Zhou et al. (1994) *J. Exp. Med.* 179:1867-1875.

Packaging cell lines suitable for use with the above-described viral and retroviral vector constructs may be readily prepared and used to create producer cell lines (also termed vector cell lines) for the production of recombinant vector particles.

Examples of non-viral methods of gene delivery vehicles and methods which may be employed according to the invention, include liposomes, nanocapsules, microparticles, lipid particles, vesicles, and the like. These non-viral methods of gene delivery are used for the introduction of the compositions of the present invention into suitable matrix, host cells/organisms. In particular, the compositions of the present invention may be formulated for delivery either encapsulated in a lipid particle, a liposome, a vesicle, a nanosphere, or a nanoparticle or the like. Alternatively, compositions of the present invention can be bound, either covalently or non-covalently, to the surface of such carrier vehicles.

The formation and use of liposome and liposome-like preparations as potential drug carriers is generally known to those of skill in the art (see for example, Wang et al., PNAS 84:7851-7855, 1987; Lasic, *Trends Biotechnol* 1998 Jul;16 (7):307-21; Takakura, *Nippon Rinsho* 1998 Mar;56(3):691-5; Chandran et al., *Indian J Exp Biol.* 1997 Aug;35(8):801-9; Margalit, *Crit Rev Ther Drug Carrier Syst.* 1995;12(2-3): 233-61; U.S. Pat. No. 5,567,434; U.S. Pat. No. 5,552,157; U.S. Pat. No. 5,565,213; U.S. Pat. No. 5,738,868 and U.S. Pat. No. 5,795,587, each specifically incorporated herein by reference in its entirety).

Other non-viral delivery methods which may be employed according to the present invention include polycationic condensed DNA linked or unlinked to adenovirus (see e.g., Curiel, *Hum. Gene Ther.* 3:147-154, 1992); ligand linked DNA, (see, e.g., Wu, *J. Biol. Chem.* 264:16985-16987, 1989); any kind of vector; deposition of photopolymerized hydrogel materials; hand-held gene transfer particle gun, as described in U.S. Pat. No. 5,149,655; ionizing radiation as described in U.S. Pat. No. 5,206,152 and WO 92/11033; and nucleic charge neutralization or fusion with cell membranes. Additional approaches are described in Philip, *Mol. Cell Biol.* 14:2411-2418, 1994, and in Woffendin, *Proc. Natl. Acad. Sci.* 91:1581-1585, 1994. Conjugates comprising a receptor-binding internalized ligand capable of delivering nucleic acids may also be used according to the present invention (see e.g., U.S. patent application Ser. No. 08/718,904). Conjugate-based preparations and methods of use thereof are described in WO 96/36362 that is hereby incorporated by reference in its entirety. Other non-viral delivery methods include, but are not limited to, mechanical delivery systems such as the approach described in Woffendin et al., *Proc. Natl. Acad. Sci. USA* 91(24):11581-11585, 1994 and naked DNA protocols. Exemplary naked DNA introduction methods are described in WO 90/11092 and U.S. Pat. No. 5,580,859.

In other embodiments, methods of the invention utilize bacteriophage delivery systems capable of transfecting eukaryotic cells. Bacteriophage-mediated gene transfer systems are described in WO 99/10014, incorporated in its entirety. Phage delivery vehicles may express a targeting ligand on their surface that facilitates receptor-mediated gene delivery.

Preparation and Implantation of the Gene-Activated Matrices

Implantable matrices may contain nucleic acid molecules that effect wound healing, tissue repair, tissue regeneration, or angiogenesis prior to implantation, or such nucleic acids may be provided to the matrix following implantation. In certain embodiments, the matrix may be conditioned prior to implantation. The matrix or implant material is contacted with nucleic acid(s) in a suitable buffer solution. Pharmaceutical grade buffers suitable for recombinant nucleic acid molecules and proteins are known in the art. The amount of nucleic acid molecules and the length of contact time required for incorporation of the nucleic acid into the matrix will depend on the structure and composition of the particular matrix employed and can be readily determined by one of ordinary skill in the art without undue experimentation.

Alternatively, nucleic acid molecules may be encapsulated within a matrix of synthetic polymers, such as, for example, block copolymers of polylactic-polyglycolic acid (See Langer and Folkman, *Nature* 263:297-800, 1976, which is incorporated by reference). The amount of biological agent to be encapsulated can be readily determined by one of ordinary skill in the art.

Biological and medical factors to be considered in determining the appropriate amount of nucleic acid applied to or incorporated within the matrix may include, for example, the particular nucleic acid, the particular promoter driving expression, the type of matrix employed, the site of the wound, the host's age, sex and diet, the medical condition being treated, the severity of the medical condition, and any other clinical factors that may effect wound healing such as serum levels of various factors and hormones and the predicted immune response. Specific factors to be considered in regard to the type of matrix employed include, for example, its size, capacity for binding or containing nucleic acids, structural stability, rate of degradation, and ability to be infiltrated by or to support repair cells.

In certain embodiments, compositions of both biological and synthetic matrices and nucleic acid molecules may be lyophilized together to form a dry pharmaceutical powder. The matrix may be rehydrated prior to implantation in the body, or alternatively, the matrix may become naturally rehydrated when placed in the body.

Gene-activated matrices may include medical devices such as, for example, stents, catheters, synthetic joints, implants and sutures. In certain embodiments of the invention, such medical devices may be coated with nucleic acids using conventional coating techniques as are well known in the art. Such methods include, by way of example and not limitation, dipping the device in the nucleic acid solution, brushing the device with the nucleic acid solution, or spraying the device with aerosol compositions comprising nucleic acids. Matrices may be dried, either at room temperature or in a drying oven, optionally at reduced pressure. In other embodiments of the invention, medical devices may be coated with a matrix composition using conventional coating techniques as known in the art, including those discussed above.

The gene-activated matrix can be transferred to the host patient by a variety of techniques. In one embodiment of the invention, the matrix can be transferred directly to the site of a naturally occurring wound or an iatrogenic injury. In certain embodiments, matrices may be surgically placed in a wound made in an organ. Matrices may also be implanted via grafting, injection, catheterization, laproscopic surgical procedures, or arthroscopic surgery. Preferred methods of implantation involving iatrogenic injury, such as injection, surgery, and arthroscopic placement, involve traversing the fluid space associated with the target tissue, thus causing minimal damage to other tissues.

In instances where the matrices are injected, the matrices may be drawn into a syringe and injected into a patient at the site of interest. Single or multiple injections may be performed at one or more sites. The amount of matrices needed to produce the desired therapeutic effect is variable depending on biological and medical factors including, but not limited to, the specific nucleic acid, the promoter driving gene expression, the particular disease and its severity, the age, weight, and medical condition of the patient, and the location of the site. The amount of matrices to implant can be readily determined without undue experimentation by clinical testing. Additionally, or alternatively, the therapeutic effect of different amounts of implanted matrix can be determined by examining clinical disease indicators, and tissue healing responses, including, but not limited to, clot formation, dissolution of the clot with concurrent removal of damaged tissue, and deposition of granulation tissue.

The present invention discloses methods, compositions and devices using both permanent and temporary gene-activated matrices. Permanent matrices that allow for the continuous administration of nucleic acids are particularly useful for treating chronic or long-term medical conditions. Efficacy of the gene-activated matrices will be examined by determining the therapeutic effect of the implanted matrices on the host patient. Clinical disease indicators and symptoms and responses can be monitored by means available to one skilled in the art.

Permanent or temporary gene-activated matrices may be recharged by applying additional nucleic acids to the matrix and/or surrounding or infiltrating cells. The additional nucleic acids may be the same as those originally applied or different. For example, if an implanted gene-activated matrix initially fails to produce or ceases producing a sufficient amount of therapeutic products, nucleic acids that promote wound healing, tissue repair, tissue regeneration, or angiogenesis may be reapplied to the matrices. Reapplication may occur by injection or by a surgical procedure. In certain instances, it is advantageous to periodically reapply nucleic acids to the matrices. In some instances, it is advantageous to provide an agent to the matrices will re-stimulate an immune response or a wound healing response. This agent may, for example, have a cytotoxic effect on cells within or associated with the gene-activated matrix, thus producing a secondary wound healing response. Alternatively, this agent may reactivate cells (e.g., repair cells) within or associated with the gene-activated matrix.

In other aspects, partitioned matrices may be created. Such partitioning may be performed by incorporating different nucleic acid molecules into differing parts of the matrix. For example, cartilage growth could be stimulated by creating a bone defect in the head of the bone and inserting a matrix having nucleic acid molecules directing the proliferation of cartilage growth or repair in one end, while the portion of the matrix exposed only to the bone may contain nucleic acid molecules directing bone repair. Such partitioning of the matrix could also be carried out by utilizing a mixture of matrix materials, such that a portion of the matrix comprises substantially one polymer, while the other portion comprises another. For instance, to facilitate differential levels of cellular infiltration, differing portions of the matrix may be made more or less porous or more or less degradable as is necessary to achieve the most efficacious tissue repair. As one of skill in the art can appreciate, any number of differing nucleic acid molecules and matrix materials may be combined to produce simple biphasic matrices as well as multipartitioned matrices. Accordingly, these matrices may be formed by one matrix composition and multiple different nucleic acid molecules, multiple matrix compositions and multiple identical nucleic acid molecules, and/or multiple matrix compositions and multiple different nucleic acid molecules.

Since the method of the invention is based on the natural migration and proliferation of cells into a wound site and into the matrix located at the wound site, followed by uptake of nucleic acids or polypeptides, it is understood that the matrices will be transferred into a tissue site in the body where the wound healing process has been induced. The local tissue damage must be sufficient to induce the wound healing response. Such a response will be induced by incisions, excisions, osteotomy, arthroscope insertion, injection, and inflammation initiated by gene-activated matrix placement.

Uses of the Gene Activated Matrix

The invention is applicable to a wide variety of clinical disease or pathological situations in which a wound site is situated in a tissue associated with a fluid space. Wounds may arise from traumatic injury, from a disease state, or from tissue damage either induced by, or resulting from, a medical procedure. The application of the invention includes, but is not limited to, bone repair, connective tissue repair, and regulation of angiogenesis, apoptosis or vasculogenesis. The method of the invention is also useful when the clinical goal is to block a disease process, thereby allowing natural tissue healing to take place.

Cartilage Repair/Regeneration

Cartilage is a specialized connective tissue that consists of chondrogenic cells dispersed within an endogenously produced and secreted extracellular matrix. In mammals, based on the amount of extracellular matrix and its organization, cartilage is categorized into three types: hyaline cartilage, fibrocartilage and elastic cartilage. Hyaline cartilage consists of a number of macromolecular components, including collagens (primarily type II collagens), proteoglycans and glycoproteins that form the extracellular matrix. It has a firm, elastic consistency and is translucent. Hyaline cartilage is predominantly found on the articulating surfaces of articulating joints and plays an important role in dissipating loads in joints and acting as a lubricant in the area of contact between the bones. It is also found in epiphyseal plates, costal cartilage, tracheal cartilage, bronchial cartilage and nasal cartilage. Fibrocartilage is essentially the same as hyaline cartilage except that it contains fibrils of type I collagen that add tensile strength to the cartilage. Fibrocartilage is commonly found in the anulus fibrosus of the invertebral disc, tendinous and ligamentous insertions, menisci, the symphysis pubis and insertions of joint capsules. Fibrocartilage acts as a transition between ligaments or tendons and bones and functions in transferring loads between ligaments or tendons and bone. Elastic cartilage is also similar to hyaline cartilage except that it contains fibers of elastin. Elastic cartilage provides flexible support to external structures and is typically present in the pinna of the ears, the epiglottis and the larynx.

Articular Cartilage Defects, Repair Responses, and Treatments

The two common types of articular cartilage defects in mammals, full-thickness and partial-thickness defects, may be caused by acute mechanical damage. The two types of defects differ not only in the extent of physical damage but also in the repair response each type of defect invokes.

Full-thickness articular cartilage defects include damage to the articular cartilage, the underlying subchondral bone tissue, and the calcified layer of cartilage between the articular cartilage and the subchondral bone. Full-thickness defects typically arise after severe trauma of the joint or during the late stages of degenerative joint diseases, such as during osteoarthritis. Since the subchondral bone tissue is both innervated and vascularized, damage to this tissue is often painful. The repair reaction induced by damage to the subchondral bone usually relies on mesenchymal cells from subchondral bone. The reparative tissue may or may not undergo metaplastic changes to form fibrocartilage at the site of the full-thickness defect, and even if fibrocartilage is formed, it typically lacks the biomechanical and mechanical properties of articular cartilage and thus degenerates with use.

Partial-thickness articular cartilage defects are restricted to the cartilage tissue itself and usually include fissures or clefts in the articulating surface of the cartilage. Partial-thickness defects are caused by mechanical arrangements of the joint which in turn induce wearing of the cartilage tissue within the joint. Soon after the injury, chondrocytes adjacent to the injured surfaces show a brief period of mitotic activity and matrix synthesis. Despite these attempts at repair, there is no appreciable increase in the bulk of cartilage matrix and the repair process is rarely effective in healing the defects.

Besides acute mechanical damage, inflammatory diseases, such as rheumatoid arthritis, may also cause articular cartilage defects. Through enzymatic pathways, inflammatory mediators may not only suppress matrix synthesis, but also lead to cartilage degradation, which eventually result in severe cartilage depletion. The capacity of cartilage and its surrounding tissues to repair the defects is inadequate against the forces of destruction directed at the cartilage.

Articular cartilage defects may also be induced by, or the result of surgical procedures. For instance, the removal of cartilage tumors, such as osteochondramya, enchondroma, periosteal chondromas and chondroblastoma, may result in cavities in the articular cartilage as well as in other cartilage tissues.

The limited capacity of articular cartilage to regenerate itself makes repair of articular defects difficult. Conventional treatment options for articular cartilage defects, such as abrasion arthroplasty, subchondral drilling, microfracture, soft-tissue arthroplasties (e.g., periosteal grafts), and osteochondral transplantation have resulted in temporary alleviation of clinical symptoms, but not in the regeneration of repair tissue with biochemical, structural, and mechanical properties similar to normal articular cartilage (Chen et al., *Am J Orthop* 26:396-406, 1997; Gilbert, *Am J Knee Surg* 11:42-6, 1998; Minas and Nehrer, *Orthopedics* 20:525-38, 1997). The limited regenerative capability of chondrocytes has thus led researchers to develop alternative treatment methods to enhance the repair response. One of such treatment methods is to introduce factors that stimulate chondrocyte progenitor cells to these cells, thus promote cartilage repair and regeneration. But these methods are less than adequate in their therapeutic benefit.

Gene-Activated Matrices for Cartilage Repair/regeneration

As a method of introducing regulatory factors that stimulate chondrocyte progenitor cells to the cells, this invention is useful in promoting cartilage repair and/or regeneration. The regulatory factors that can be used in this invention includes, but are not limited to, systemic hormones, growth factors and other proteins that regulate proliferation and differentiation of cells. Growth factors, hormones and other proteins reported to have such cartilage-repairing capacity include, for example, the fibroblast growth factors (FGF), insulin-like growth factors (IGF), IGF receptors, hepatocyte growth factor (HGF), transforming growth factors (e.g., TGFα and TGFβ), platelet derived growth factor (PDGF), activins, inhibins, parathyroid hormone-related peptide (PTHrP), parathyroid hormone (PTH), leukemia inhibitory factor (LIF), skeletal growth factor (SGF), connective tissue growth factors (CTGF) (e.g., CTGF-1 disclosed in U.S. Pat. No. 5,408, 040, and CTGF-2 disclosed in PCT publication WO 96/01896), epidermal growth factor (EGF), bone morphogenetic proteins (BMPs) (e.g., BMP1, BMP2, BMP3, BMP4, BMP5, BMP6, and BMP7 disclosed in U.S. Pat. Nos. 5,108, 922, 5,013,649, 5,116,738, 5,106,748, 5,187,076, and 5,141, 905; BMP8 disclosed in PCT publication WO94/26892; BMP9 disclosed in PCT publication WO 93/00432; BMP10 disclosed in PCT publication WO94/26893, BMP11 disclosed in PCT publication WO 94/26892, BMP12, BMP13 disclosed in PCT publication WO 95/16035), MBP receptors (Reddi, *Matrix Biol.* 14:599, 1994), BIP (disclosed in WO 94/01557), MP52 (disclosed in WO93/16099), chondromodulins (e.g., chondromodulin-I, chondromodulin-II, and chondromodulin-III) (Suzuki, *Biochem. Biophys. Res. Comm.* 259:1, 1999) and cartilage morphogenetic proteins (CDMPs) (Reddi, *Matrix Biol* 14:599-606, 1994, Luyten, Int. *J. Biochem. Cell Biol.* 29:1241, 1997). The nucleic acids encoding the above proteins and any other proteins (including proteins both currently known and identified in future) having the capacity to stimulate cartilage progenitor cells or promote cartilage repair and/or regeneration can be used for the preparation of the gene-activated matrices of this invention. Proteins that activate the production and secretion of such proteins may also be used with the gene activated matrices of the present invention. These include transcription factors and zinc-finger binding proteins. Such factors could bind DNA and protect it. Many proteins have been identified that bind specific sequences of DNA. These proteins are responsible for genome replication, transcription and repair of damaged DNA. The transcription factors regulate gene expression and are a diverse group of proteins. These factors are especially well suited for purposes of the subject invention because of their sequence-specific recognition. Host transcription factors have been grouped into seven well-established classes based upon the structural motif used for recognition. The major families include helix-turn-helix (HTH) proteins, homeodomains, zinc finger proteins, steroid receptors, leucine zipper proteins, the helix-loop-helix (HLH) proteins, and β-sheets. Other classes or subclasses may eventually be delineated as more factors are discovered and defined. Proteins from those classes or proteins that do not fit within one of these classes but bind nucleic acid in a sequence-specific manner, such as SV40 T antigen and p53 may also be used.

These families of transcription factors are generally well-known (see GenBank; Pabo and Sauer, *Ann. Rev. Biochem.* 61:1053-1095, 1992; and references below). Many of these factors are cloned and the precise DNA-binding region delineated in certain instances. When the sequence of the DNA-binding domain is known, a gene encoding it may be synthesized if the region is short. Alternatively, the genes may be cloned from the host genomic libraries or from cDNA libraries using oligonucleotides as probes or from genomic DNA or cDNA by polymerase chain reaction methods. Such methods may be found in Sambrook et al., supra.

Helix-turn-helix proteins include the well studied λ Cro protein, λcI, and *E. coli* CAP proteins (see Steitz et al., *Proc. Natl. Acad. Sci. USA* 79:3097-3100, 1982; Ohlendorf et al., *J. Mol. Biol.* 169:757-769, 1983). In addition, the lac repressor (Kaptein et al., *J. Mol. Biol.* 182:179-182, 1985) and Trp repressor (Scheritz et al., *Nature* 317:782-786, 1985) belong to this family. Members of the homeodomain family include the Drosophila protein Antennapaedia (Qian et al., *Cell.* 59:573-580, 1989) and yeast MAT α2 (Wolberger et al., *Cell.* 67:517-528, 1991). Zinc finger proteins include TFIIIA (Miller et al., *EMBO J.* 4:1609-1614, 1985), Sp-1, zif 268, and many others (see generally Krizek et al., *J. Am. Chem. Soc.* 113:4518-4523, 1991). Steroid receptor proteins include receptors for steroid hormones, retinoids, vitamin D, thyroid hormones, as well as other compounds. Specific examples include retinoic acid, knirps, progesterone, androgen, glucocosteroid and estrogen receptor proteins. The leucine zipper family was defined by a heptad repeat of leucines over a region of 30 to 40 residues. Specific members of this family include C/EBP, c-fos, c-jun, GCN4, sis-A, and CREB (see generally O'Shea et al., *Science* 254:539-544, 1991). The helix-loop-helix (HLH) family of proteins appears to have some similarities to the leucine zipper family. Well-known members of this family include myoD (Weintraub et al., *Science* 251:761-766, 1991); c-myc; and AP-2 (Williams and Tijan, *Science* 251:1067-1071, 1991). The β-sheet family uses an antiparallel β-sheet for DNA binding, rather than the more common α-helix. The family contains the MetJ (Phillips, *Curr. Opin. Struc. Biol.* 1:89-98, 1991), Arc (Breg et al., *Nature* 346:586-589, 1990) and Mnt repressors. In addition, other motifs are used for DNA binding, such as the cysteine-rich motif in yeast GAL4 repressor, and the GATA factor. Viruses also contain gene products that bind specific sequences. One of the most-studied such viral genes is the rev gene from HIV. The rev gene product binds a sequence called RRE (rev responsive element) found in the env gene. Other proteins or peptides that bind DNA may be discovered on the basis of sequence similarity to the known classes or functionally by selection.

Any matrix that is bio-compatible can be used for the preparation of the gene-activated matrices in treating cartilage defects. The matrix should have minimum histotoxicity and is not carcinogenic. The matrix preferably possesses appropriate mechanical and physical properties suitable for the functions of normal cartilage. It can either be biodegradable or not biodegradable. In some embodiments, the matrix is flexible and the shape of the matrix may be manipulated to restore the original shape of cartilage surfaces. It can also be made from a component of natural cartilage, such as collagen, especially type II collagen.

Gene-activated matrices having nucleic acids that promote cartilage repair and/or regeneration or stimulate cartilage progenitor cells can be implanted in cartilage defective sites or cartilage progenitor sites. Methods of implantation include, for example, using an arthroscope and injection. Preferred methods of implantation will be minimally invasive. For full-thickness articular cartilage defects, gene-activated matrices that promote both cartilage and bone repair and/or regeneration may be implanted partially into the existing wound site or into a wound site created for matrix implantation such as a core defect of the subchondral bone and partially into the defective site of the cartilage. For partial-thickness articular cartilage defects, a gene-activated matrix can be implanted directly into the defective cartilage (e.g., existing wound) or into a wound site created for matrix implantation. In this situation, adhesive matrices (i.e., matrices having adhesive materials to keep the matrices attached to the defective cartilage site) are preferred. Alternatively, a wound in the subchondral bone beneath the defective cartilage may be created, and gene-activated matrices similar to those used for treating full-thickness articular cartilage defects can be partially implanted into the wound site of the subchondral bone and partially into the defective site of the cartilage. The portion of the gene-activated matrices implanted in the cartilage defective site may be made of the same material or a different material as that implanted in the subchondral bone wound site. The nucleic acids of the portion of the matrices implanted in the cartilage defective site may be the same or different from those in the subchondral bone wound site (e.g., BMP genes and CDMP genes encoding protein that promote both bone and cartilage repair and/or regeneration). For instance, the nucleic acids of the portion of the matrices implanted in the cartilage defective site promote cartilage repair and/or regeneration, while the nucleic acids of the portion of the matrices implanted in the subchondral bone wound site promote bone repair and/or regeneration. Nucleic acids that promote bone repair and/or regeneration are well known in the art, including, but not limited to, BMP genes, CDMP genes, TGF genes, FGF genes, granulocyte/macrophage colony stimulating factor (GM-CSF) genes, EGF genes, PDGF genes, IGF genes, LIF genes.

One of ordinary skill in the art should recognize that this invention is not limited to the treatments of articular cartilage defects; it is also useful in treating defects of other types of cartilage, such as fibrocartilage, elastic cartilage, and hyaline cartilage. Accordingly, gene-activated matrices of this invention may be used to promote the wound healing and tissue regeneration of all types of cartilage.

Gene-Activated Matrices for Treating Arthritis

Arthritis is a crippling disease that incapacitates millions of people. The two most common forms of arthritis are osteoarthritis (OA) and rheumatoid arthritis (RA). OA is the most common form of all articular disorders and first appears asymptomatically between age 20 and 30 and becomes universal by age 70. OA is not characterized by extreme inflammation. The onset of OA is subtle and gradual, usually involving one to a few joints. As the disease progresses, cartilage becomes degraded, joint motion becomes diminished, flexion contractures occur, tenderness and grading sensations appear.

In contrast to OA, inflammation is commonly associated with RA. During RA, progressive joint inflammation results in irreversible cartilage destruction, leading to erosion of articular cartilage, injury of surrounding tissues and eventually permanent loss of joint function (Verschure et al., *Histochem. J.* 28:835, 1996). The pathological cartilage destruction are the result of increased degradation of articular cartilage, reduced matrix synthesis and chondrocyte death. Synovial cells, chondrocytes, macrophages and lymphocytes that infiltrate arthritic joints, generate large quantities of mediators during inflammation. These mediators include cytokines (e.g., IL-1, IL-6, IL-8, TNF-$\alpha$, GM-CSF), proteolytic enzymes (e.g., metalloproteinases such as collagenase and stromelysin, cysteine and serine proteinases, aggrecanase) and reactive oxygen species (e.g., nitric oxide produced by nitric oxide synthase). In addition, chronic interference with factors that upregulate synthesis of matrix components in chondrocytes play an important role in cartilage destruction during joint inflammation.

This invention may be useful in treating arthritis in several ways. Gene-activated matrices comprising nucleic acids that promote cartilage growth, repair or regeneration (discussed above) can be used to decrease or prevent cartilage destruction. Nucleic acids encoding for factors capable of directly antagonizing cytokine action, either by blocking cytokine-receptor binding, inhibiting local cytokine synthesis, or complexing the cytokine into an inactive form, can also be used for the preparation of gene-activated matrices (Pelletier et al., Semin. *Arthritis Rheum.* 6 Suppl.:12, 1991). For instance, IL-4 has been demonstrated to suppress the synthesis of IL-1, TNF-$\alpha$ and thus prevents collagen and proteoglycan breakdown in articular cartilage (U.S. Pat. No. 5,679,338). The nucleic acids used in the treatment of arthritis also include, but are not limited to, (1) ribozymes that cleave mRNAs for inflammation mediators (e.g., IL-1, IL-6, IL-8, TNF-$\alpha$, GM-CSF), for proteolytic enzymes (e.g., metalloproteinases such as collagenase and stromelysin, cystein and serine proteinases, aggrecanase), and for nitric oxide synthase, (2) DNAs encoding these ribozymes, and (3) antisense nucleic acids that bind to mRNAs for inflammation mediators, proteolytic enzymes and nitric oxide synthase. Other nucleic acids used in the treatment of arthritis also include, but are not limited to, DNAs encoding Tissue Inhibitors of Metalloproteinasess (TIMPs) and transcription factors that activate their expression, DNAs encoding soluble receptors for the above-mentioned cytokines and transcription factors that activate their expression, DNAs encoding monoclonal antibodies that bind to the above mentioned cytokines and proteolytic enzymes, DNAs encoding factors involved in cell survival (such as BCL-2) and the transcription factors involved in their expression, and DNAs encoding zinc finger binding proteins for the above mentioned soluble receptors, TIMPs and cell survival factors.

Regulation of Angiogenesis

The present invention may also be used to regulate the formation and spreading of blood vessels, or vasculogenesis and angiogenesis, respectively. Both these physiological processes play an important role in wound healing and organ regeneration.

Initially, at the site of a wound, granulation tissue which is a mixture of collagen, matrix and blood vessels, is deposited and provides wound strength during tissue repair. The formation of new blood vessels involves the proliferation, migration and infiltration of vascular endothelial cells, and is known to be regulated by a variety of polypeptide growth factors. Several polypeptides with endothelial cell growth promoting activity have been identified, including acidic and basic FGF, vascular endothelial growth factor (VEGF), TGFs (TGF$\alpha$ and TGF$\beta$), TNF-$\alpha$, HGF, and placental derived growth factor (PDGF).

To stimulate the formation and spreading of blood vessels, nucleic acids encoding such growth factors may be incorporated into matrices and these matrices may be implanted into the host. In some instances, it may be necessary to induce the wound healing process through tissue injury.

It may be desirable to inhibit the proliferation of blood vessel formation, such as in angiogenesis associated with the growth of solid tumors that rely on vascularization for growth. Tumor angiogenesis may be inhibited through the transfer of nucleic acids encoding angiogenesis inhibitors, such as thrombospondin or angiostatin. In specific embodiments of the invention, nucleic acids encoding angiogenesis inhibitors may be incorporated into a matrix followed by implantation of the matrix into a patient at the site of the tumor.

Gene-Activated Matrices for Treating Ischemic Heart Disease

This invention can also used in the treatment of ischemic heart disease either alone or in combination with transmyocardial revascularization procedures, including transmyocardial laser revascularization. Ischemic heart disease is the most common cause of death in the United States and the world. Each year in the United States, one and a half million people have a myocardial infarction and half a million die as a result. One of the symptoms of ischemic heart disease is angina pectoris, which results from an imbalance between myocardial oxygen supply and demand. Although medical and surgical therapy is often successful in restoring this balance to the ischemic myocardium, there is a large number of patients that cannot benefit from more conventional therapies, such as percutaneous transluminal coronary angioplasty or coronary artery bypass grafting. To these patients, transmyocardial revascularization has emerged as a promising alternative therapy. Transmyocardial revascularization is a procedure to create transmural channels that presumably allow oxygenated ventricular blood to bathe the ischemic areas of myocardium. The effectiveness of this treatment may be due to its evocation of an angiogenic response and thereby improving local perfusion to ischemic myocardial territories.

Ischemia and infarction are examples of tissue injury, and as such represent wound environments in which wound repair cells are present. Their presence is part of a biological response aimed at repairing tissue injury, by actions such reversing tissue ischemia (through the induction of neovascularization), removal of dead or dying cells, and both collagen deposition and scar remodeling. Therefore, when GAMs are directly injected into ischemic or infarcted tissues, wound repair cells will be present in the general delivery area. In addition, direct injection using a needle or syringe will induce further tissue injury directly at the injection site, and therefore further enhance the influx of wound repair cells into this environment. Wound repair cells by nature are efficient at gene vector uptake and transgene expression, and will therefore allow for expression of the transgene product(s) encoded within the GAMs of the present invention If the transgene products encode factors aimed at enhancing tissue repair, or limiting cellular death, or influencing collagen deposition or scar formation, or inducing other processes aimed at reversing tissue injury, then an overall beneficial effect can be achieved within the treated tissues. For example, growth factors that induce neovascularization would help reverse tissue ischemia, growth factors that induce cell migration and/or mitogenesis would help repair tissue damage, adhesion molecules that induce cellular invasion and/or activation would enhance wound cell recruitment and activity, cellular receptors that encode growth factor receptors would help increase cellular responsiveness and activities, proteins that act as anti-apoptotic or pro-survival factors would help limit tissue injury, and factors that influence collagen deposition and/or scar remodeling would help remodel tissue into a more functional state.

To stimulate the growth of collateral blood vessels from occluded stem arteries to reentrant vessels downstream from the site of vascular obstruction, nucleic acid-activated matrices having nucleic acids encoding for angiogenic factors (e.g., FGF, VEGF, TGF, TNF-α, HGF, PDGF) may be implanted to an ischemic region of the heart. The implantation can be made by first creating a transmyocardial channel in the ischemic region using lasers, power drills or other means. The gene-activated matrices may be subsequently inserted into the transmyocardial channels.

Alternatively, it should be noted that this invention may also be used in treating ischemic heart disease in the absence of transmyocardial revascularization. Gene-activated matrices having nucleic acids encoding for angiogenic factors may be implanted to ischemic region of the heart by injection or administration to a freshly-created wound site other than transmyocardial channels in the ischemic region.

For delivery of the GAMs to ischemic or infarcted tissue, an illustrative delivery device is capable of direct injection into ischemic or infarcted tissue. Its design may vary from a standard syringe and needle, to a specific device designed for this purpose (for example, a device incorporating multiple needles in a set pattern, a device incorporating both needles and an energy generating system such as lasers or radio frequency energy sources or heat sources aimed at increasing local tissue injury, or a device incorporated needles and mechanical components such as drills or air jets aimed at increasing local tissue injury). Delivery in the present invention may be directly into ischemic or infarcted tissue. This could be achieved either through intraoperative routes or precutanous routes. The target tissues of the present invention may be ischemic or infarcted. While these situations would be most commonly encountered in skeletal muscle (in the case of lower limb or peripheral ischemia) and myocardium (in the case of coronary artery disease, ischemic heart disease, myocardial infarction, etc.), it can occur in any tissue or organ deprived of an adequate blood supply. This includes organs with limited blood supplies as a result of pathological conditions (e.g., atherosclerosis, disseminated intravascular coagulation or DIC, stroke, etc.), or as a result of physical or surgical trauma, or as a result of ongoing biological processes (e.g., the development of tumors with low oxygen tension or necrotic centers).

Gene-Activated Matrices for Treating Solid Tumors

Solid tumor growth is supported by blood vessel formation within the tumor. A variety of treatment methods attempt to halt tumor growth by inhibiting angiogenesis, and thus depriving tumor tissue of its oxygen supply. The methods and compositions of the current invention may be used to inhibit angiogenesis within tumors associated with a fluid space. Gene-activated matrices containing nucleic acid encoding an angiogenesis inhibiting factor, such as angiostatin or thrombospondin-2, can be implanted within the tumor. Tumor cells and infiltrating repair cells will incorporate and express the angiogenesis inhibiting factor, thus slowing or halting tumor growth.

EXAMPLES

Example 1

New Tissue Formation in vivo Within a Biocompatible Substance

PVA sponges were implanted subcutaneously into rats on day 0 and injected on day 4 with collagen containing $10^9$ pfu adenovirus encoding luciferase (AdLuc) (Rogers et al., Tumor Targeting 3:25-31, 1998) or PDGF-BB (AdPDGF) (Liechty et al., J. Invest. Dermatol. 113(3):375-383, 1999). It should be noted that at 4 days this is a fluid filled space. At day 10 post-implantation, sponges were removed and processed. Expression of PDGF-BB was confirmed by ELISA.

Sections were stained with Alcian blue to detect infiltrating cells and glycosaminoglycans or Sirius red to detect mature collagen bundles. As demonstrated in FIG. 1, increased cellularity and vascularity present were observed in AdPDGF sponges as compared to sponges injected with AdLuc.

Formalin-fixed, paraffin-embedded sponge sections were stained using Masson's Trichrome. Image-Pro Plus software (Media Cybernetics, Silver Spring, Md.) was used to differentiate new tissue from sponge matrix based on pixel density. Percent new tissue area/total area was calculated as approximately 25% for collagen containing AdLuc and 60% for collagen containing AdPDGF.

Example 2

Bone Healing in Lower Limbs of Horses

Eight healthy (CBC, Chemistry profile and physical exam), sound (radiographs, lameness evaluation and joint assessment) adult (age 3-15 yrs) horses undergo arthrotomy under general anesthesia of the metacarpus III (MCIII) and metacarpophalangeal (MCP) joint of each limb. On Day 0 one randomly assigned limb has 2 p-MAT gene coated collagen sponges placed, one through a small hole drilled into diaphyseal cortex of the dorsal MCIII and the other through the distal condyle of MCIII in the MCP joint. The contralateral limb undergoes arthrotomy of the same sites but will serve as a control. With forceps, sponges are placed through a small stab incision (~½cm) into the areas mentioned above and closed with a single suture. Subsequently, the horses are dosed with phenylbutazone once a day (2.2 mg/kg) IV and bandaged for 3 days while housed in 12'×12' box stalls. Here they remain for 4 weeks. During the first week post-op, daily evaluations are performed including temperature, heart rate, respiratory rate and time in recumbancy. At week 1 the following parameters are assessed: radiographic images of MCIII and MCP, synovial fluid analysis, joint circumference, lameness evaluation and bloodwork. From week 2- week 4, weekly evaluations are performed. At week 4, the above-noted parameters are assessed again and at this time the horses are turned out to paddock together. Parameters are assessed at week 8, and finally at week 12. Between week 12 and week 13 horses are euthanized for necropsy and histologic evaluation. MCIII is harvested after euthanasia and CT scans taken of the healing defects to assess mineralization. Bone slabs (2 mm thick) through the center of the defect are obtained and high detail radiography performed to assess mineralization and organization. Defects are decalcified and sectioned for histologic assessment of number of osteons per unit area (osteonal density), osteonal activity, and mineral oppositions rate.

Example 3

Collagen-Immobilized FGF Genes Induce Angiogenesis in vivo

METHODS: DNA-matrix formulations. Eukaryotic expression plasmids were constructed encoding either firefly luciferase ($DNA_{Luc}$), an 18 kD mutein of FGF2 in which the cysteine at position 96 has been engineered to a serine ($DNA_{FGF2}$), or a 23 kD form of FGF6 ($DNA_{FGF6}$); all transgenes were under control of the CMV promoter. Although lacking a classic signal peptide sequence, the FGF2 transgene product is efficiently exported from transfected cells by a signal sequence-independent but energy-dependent pathway (Florkiewicz, R. Z., et al., 1995. J. Cell Physiol. 162:388-399). Recombinant FGF2 mutein protein was also produced as previously described (Sosnowski, B. A., et al., 1996 J. Biol. Chem 271:33647-33653), and demonstrated equivalent activity to wild type 18 kD FGF2 in endothelial proliferation assays (Sosnowski, B. A., et al., 1996 J. Biol. Chem 271: 33647-33653). Adenovirus vectors, for example, AdFGF2 and AdFGF6, were also constructed and used at $5 \times 10^{10}$ virus particles/wound. Plasmids and recombinant FGF2 and FGF6 were formulated in matrices prepared from admixtures of bovine type I collagen (Matrix Pharmaceutical, San Diego, Calif.) and gelatin (prepared by heating collagen at 56° C. for 20 min). The following reagent concentrations were selected for in vivo studies, based on their ability to form stable, single-phase formulations: 0.6 or 1% collagen, 1% gelatin, 20 mg/ml DNA, and 1.2 mg/ml FGF2 protein.

Collagen solution was prepared on ice as follows: 1 mg/ml bovine type I collagen (Cohesion Technologies, Palo Alto, Calif.), 1× MEM (GIBCO/BRL, Grand Island, N.Y.), 2.2 mg/ml $NaHCO_3$, 10% FBS, and plasmid DNA at 12 pg/ml. Following pH adjustment to ~7.4, collagen solutions were aliquoted as 500 μl per 24-well cluster plate well. A single 1 $mm^2$ piece of left ventricle freshly isolated from rat heart was added to each well, and the collagen solution gelled by incubation at 37° C. for 30 min. Gels were then overlaid with culture medium (DMEM containing 10% FBS), and microvascular outgrowth assessed at various times using routine immunohistochemistry. Briefly, gels were rinsed with PBS, incubated with biotinylated BSL-I lectin, rinsed with PBS, incubated with streptavidin-FITC, rinsed with PBS, and finally covered with PBS containing the DNA stain DAPI (all reagents from Vector Laboratories, Burlingame, Calif.). When viewed using an inverted fluorescent microscope, this procedure allows visualization of both endothelial cells (green cytoplasmic fluorescence) as well as total cells (blue nuclear fluorescence).

Figure 2:
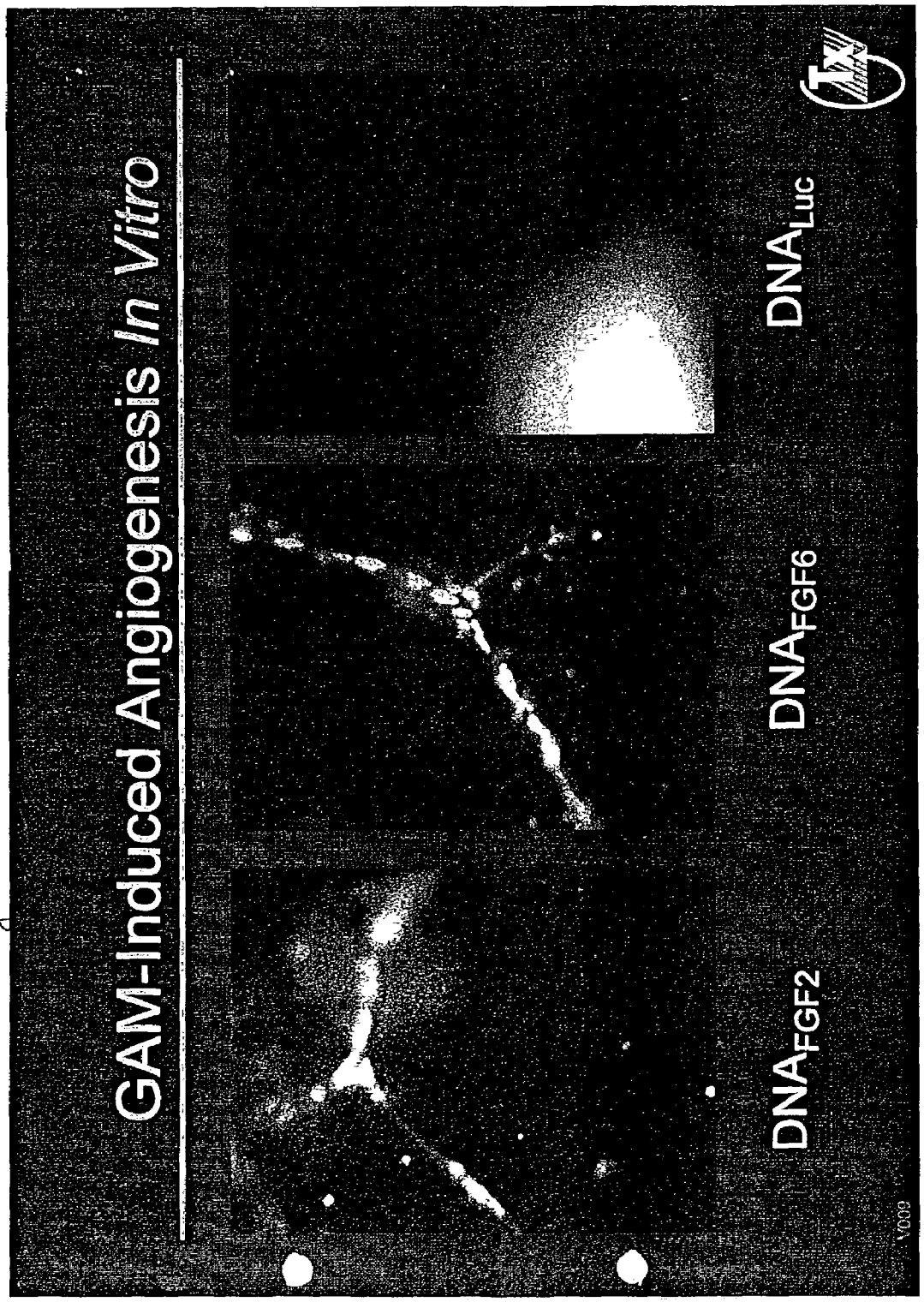
FIG. 2 is a photograph following immunohistochemistry showing that 3-dimensional cultures that were formulated to contain plasmid DNA encoding the non-angiogenic gene luciferase, capillary sprouting did not initiate from myocardial fragments. By contrast, classic in vitro angiogenesis was observed when FGF2 or FGF6 genes were used (left 2 panels). By day 14 of culture, numerous branching microvascular networks were observed arising from heart fragments and extending throughout the collagen gels. used (left 2 panels). By day 14 of culture, numerous branching microvascular networks were observed arising from heart fragments and extending throughout the collagen gels.

RESULTS: Given the correct stimulatory conditions, angiogenesis can be recapitulated in vitro using either cultured endothelial cells or vascularized tissue fragments as described above. Therefore, in order to confirm the activity of the genematrix materials, organ cultures were established by embedding fragments of rat myocardium in 3-dimensional collagen gels, and followed microvascular sprouting by immunohistochemistry (FIG. 2).

When 3-dimensional cultures were formulated to contain plasmid DNA encoding the non-angiogenic gene luciferase, capillary sprouting did not initiate from myocardial fragments. By contrast, classic in vitro angiogenesis was observed when FGF2 or FGF6 genes were used (FIG. 2). By day 14 of culture, numerous branching microvascular networks were observed arising from heart fragments and extending throughout the collagen gels. The endothelial-reactive lectin BSL-I confirmed that these structures were formed from chains of individual endothelial cells. Using this in vitro assay system, therefore, collagen-immobilized FGF genes induce an angiogenic response from muscle tissue.

Example 4

Collagen Matrices are Retained at Delivery Sites in Skeletal Muscle

Rodent hindlimb model: Excisional defects were created in the quadriceps muscles of Sprague-Dawley rats by blunt dissection of the hindlimb skin, resection of the overlying tensor muscle, and removal of plugs (3 mm diameter×5 mm depth) from rectus femoris muscles using tissue biopsy punches. DNA-matrix formulations as described herein and in Example 3 were then injected into these defects as 50 μl volumes using a 27-gauge catheter-sheathed needle, after which rectus wounds and tensor muscles were repaired with sutures, and overlying skin closed with wound clips. In some studies, DNA-matrix was also delivered to intact muscles (without previous creation of excisional defects) by direct injection through a 27-gauge needle, in order to deliver genes to a minimally wounded environment.

At the desired assay times, treatment areas were harvested, tissues were fixed in 0.4% paraformaldehyde in Sorenson's phosphate, and paraffin embedded. For routine morphological assessment, paraffin sections were stained according to either hematoxylin/eosin or Masson's trichrome protocols. For detection of smooth muscle cell-containing blood vessels, sections were immunohistochemically stained with mouse anti-α-actin (clone 1A4, Dako, Carpinteria, Calif.), followed by HRP-labeled anti-mouse IgG and DAB (Vector Laboratories). For detection of regenerating myocytes, mouse anti-neural cell adhesion molecule (N-CAM, CD56) was used as the primary antibody (Chemicon, Temecula, Calif.). Finally, tissue sections were photographed as non-overlapping microscopic fields, and an image analysis software package (Image-Pro Plus, Media Cybernetics, Silver Spring, Md.) was used to quantify DAB reaction product area. Data are represented as the total area of positive DAB staining per wound site (n=6 wounds, and 15-20 microscopic fields).

Statistical Analyses: Groups of three or more means were compared using one-way ANOVA and Fisher's procedure for least significant differences (StatView software, Abacus Concepts, Berkeley, Calif.).

RESULTS: To directly test the concept that DNA-matrix formulations will be well retained at delivery sites, plugs from rat quadriceps muscles were surgically removed and then filled these defects with test formulations as described above. Plasmid DNA concentrations were 20 mg/ml, and Evan's blue was added as a visual marker. Six hours after animals were recovered from anesthesia, quadricep muscles were harvested and examined for residual material.

Figure 3:
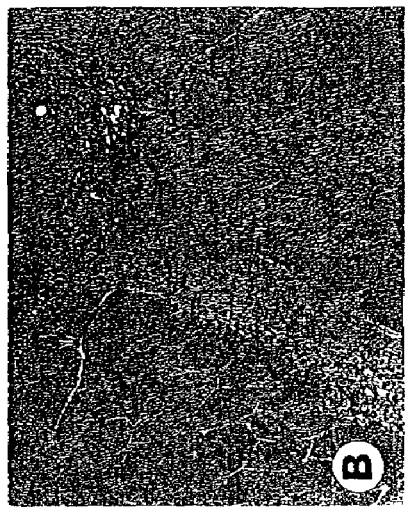
FIG. 3, panels A, B, and C: Panels A and B are micrographs at 100×magnification of skeletal muscle wounds following injection of plasmid DNA formulated in either saline (A) or 0.6% collagen (B). Excisional defects were created in rat quadriceps muscles, and then filled with plasmid DNA formulations as described. Animals were then recovered from anesthesia, and six hours later quadriceps were harvested and processed as hematoxylin/eosin-stained paraffin sections. Panel C: Adenovirus encoding luciferase was formulated in either gelatin or gelatin-collagen admixtures of various concentrations, and then delivered to rectus muscle wounds as $5 \times 10^{10}$ virus particles/wound. At 6 days post-delivery, tissue lysates were prepared from treated muscles, and both luciferase activity and protein content determined. Data are presented as pg luciferase/gg protein (mean±SD, n=3).
Figure 3:
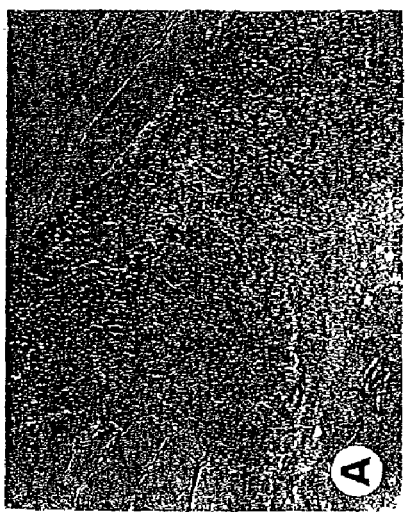
Figure 3:
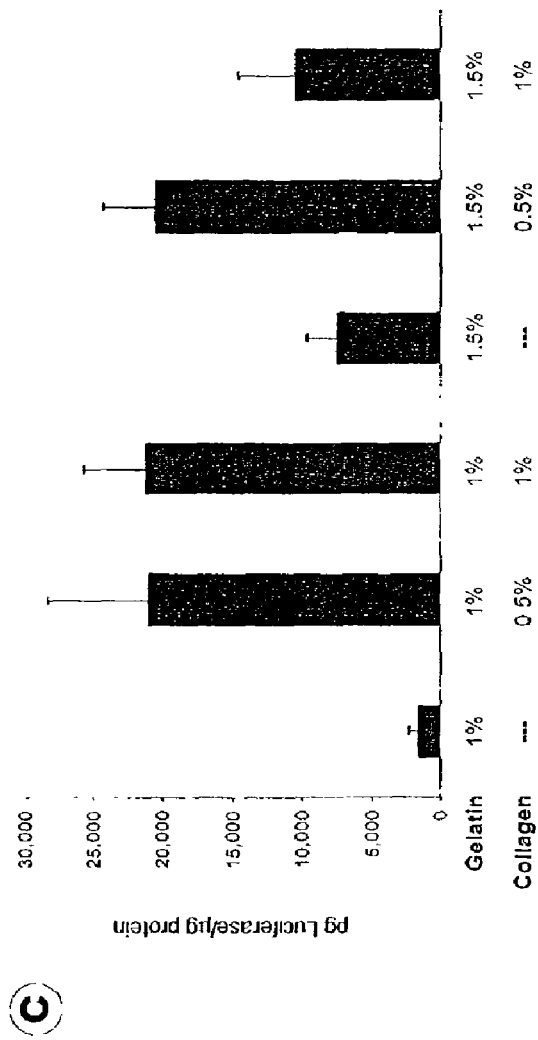

Hematoxylin/eosin-stained sections reveal that, following its delivery, a formulation of DNA and 0.6% collagen remains well localized at delivery sites. A more complex mixture consisting of plasmid DNA, 1% collagen, and 1% gelatin was similarly well retained within muscle defects. In addition, both formulations were infiltrated by mononuclear cells, indicating that these materials were conducive to cell migration and adhesion. This is important in that the present gene therapy design aims to transfect wound repair cells that migrate into vector-matrix formulations. In contrast to these observations, plasmid DNA formulated in saline was not retained within muscle wounds. By six hours post-delivery, saline-formulated DNA was no longer retained within muscle wounds (FIG. 3A). Rather, the wounds were completely filled with clotted blood. By contrast, DNA formulated in 0.6% collagen remained well localized at delivery sites (FIG. 3B). In addition, collagen-based matrices were infiltrated by mononuclear cells as early as 6 hours post-delivery, confirming that these materials were conducive to cell migration. As shown in FIG. 3C, higher luciferase expression was achieved using 1.5% collagen vs. 1% collagen as the carrier matrix. Admixtures of collagen and gelatin performed even better than collagen alone, as long as total protein concentration was held to 2%. Therefore, equivalent luciferase expression was seen using either 1% collagen-0.5% gelatin, 1% collagen-1% gelatin, or 1.5% collagen-0.5% gelatin. Histologic assessment of these materials revealed that enhanced cellular infiltration paralleled enhanced transgene expression (data not shown), suggesting that collagen/gelatin-based matrices influence transgene expression by allowing more or less wound repair cells to encounter the incorporated vectors. Overall, the data show that, within limits, there is flexibility in the design of suitable matrices for gene delivery.

Example 5

FGF Gene Delivery to Skeletal Muscle Wounds Induces Both Angiogenesis and Arteriogenesis The influence of collagen-immobilized FGF genes on muscle wound repair was examined using the rodent hind limb model described in Example 4. Three separate gene-encoding plasmids were used for this work, one gene well documented to induce angiogenesis (FGF2), one relatively little studied (FGF6), and PDGF-B.

Figure 4:
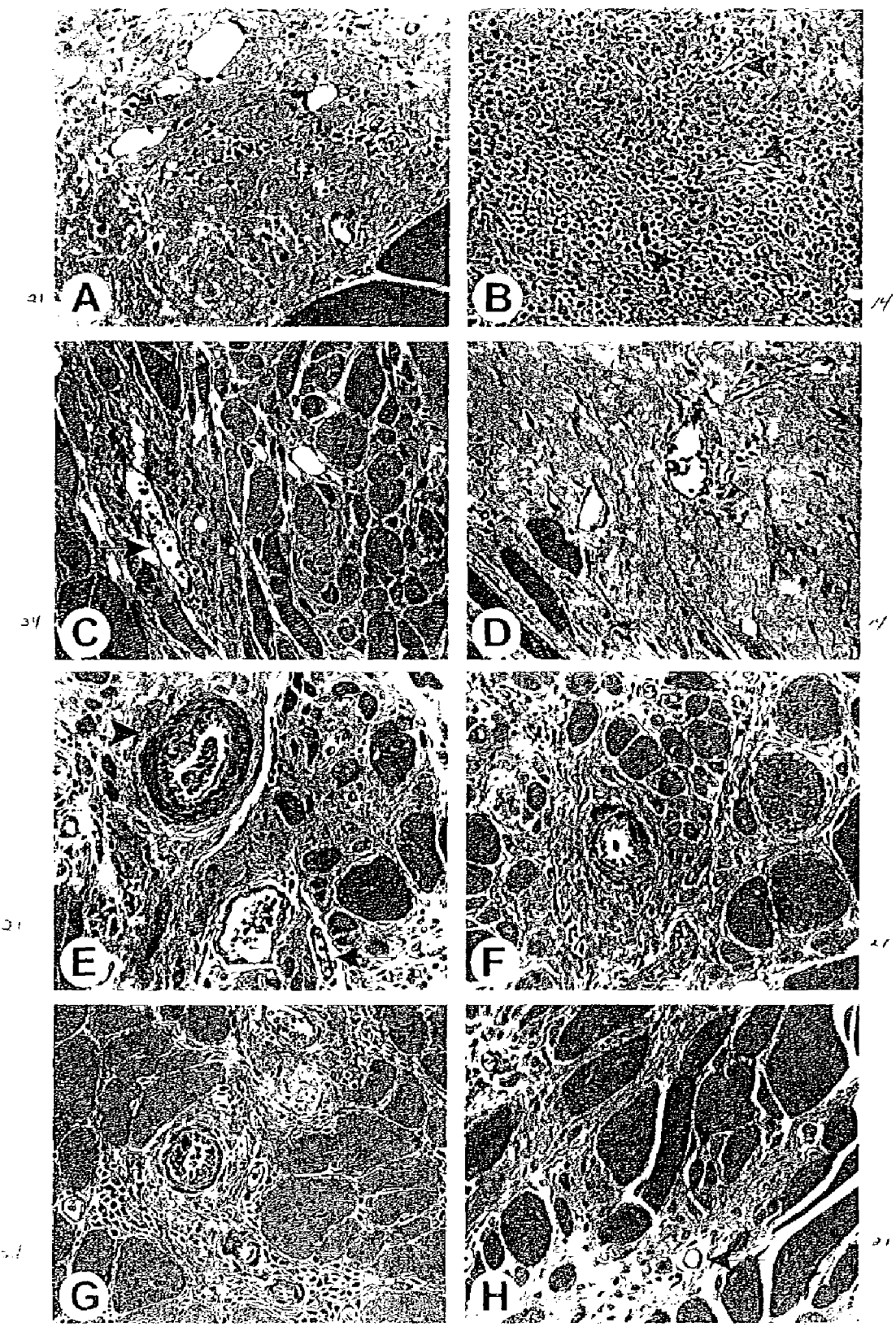
FIG. 4, panels A-H, are micrographs showing matrix remodeling following delivery to muscle wounds. Excisional defects were created in rat quadriceps muscles, and then injected with either plasmids encoding luciferase (A), PDGF-B (B&C), FGF2 (D&E), or FGF6 (F), or adenovirus encoding FGF2 (G), or FGF2 protein (panel H). All treatments were formulated in a 1% collagen-1% gelatin admixture; plasmids were delivered as 1 mg, adenovirus as $5 \times 10^{10}$ virus particles, and FGF2 protein as 60 μg per wound. At either days 14 (B&D), 21 (A, E-H), or 34 (C) post-treatment, wound sites were harvested and stained according to Masson's trichrome procedure. Arrows point to microvasculature, arrowheads to muscular arterioles. Original magnifications for all images were 400×.

As is shown in FIG. 4, excisional defects were created in rat quadriceps muscles, and then injected with either, plasmids encoding luciferase (A), PDGF-B (B&C), FGF2 (D&E), or FGF6 (F), or adenovirus encoding FGF2 (G), or FGF2 protein (panel H). All treatments were formulated in a 1% collagen-1% gelatin admixture; plasmids were delivered as 1 mg, adenovirus as $5 \times 10^{10}$ virus particles, and FGF2 protein as 60 µg per wound. At either days 14 (panels B & D), 21 (panels A and E-H), or 34 (panel C) post-treatment, wound sites were harvested and stained according to Masson's trichrome procedure. Arrows point to microvasculature, arrowheads to muscular arterioles. Original magnifications for all images were 400x. At day 14 following delivery of $DNA_{FGF2}$ formulated in a blend of 1% collagen and 1% gelatin, trichrome stains revealed that these matrices were well infiltrated by both mononuclear cells and elongated fibroblastoid cells. Many of these cells were organized around simple single-walled vessel, and may represent vascular precursors giving rise to neovasculature. The presence of erythrocytes with vessel lumens confirmed that these vessels were perfused. By day 21 post-treatment, in addition to microvasculature, well-organized muscular arterioles were also present. Skeletal muscle bundles were scattered throughout the collagen-gelatin matrix, which appeared to be reduced in volume over that seen at day 14. Neither the residual matrix nor the surrounding tissue showed any signs of edema. Very similar observations were seen following the delivery of collagen-gelatin-$DNA_{FGF6}$ to muscle wounds, including the development of both micro- and macrovasculature.

In contrast to these FGF gene-induced responses, delivery of the control transgene luciferase induced a much different response. Even at day 21, considerable collagen-gelatin matrix remained, and although a mononuclear cell infiltrate was present, blood-perfused vessels perfused were rare. Infiltrating cells were organized into discrete areas, within which the collagen-gelatin matrix appeared to have been digested away, however the majority of these structures were not true vasculature in that they were not lined by a continuous endothelium and were not perfused with blood. Finally, delivery of FGF2 protein was seen to induce a limited angiogenic response comprised of small capillaries. Arteriogenesis similar to that induced by FGF2 or FGF6 gene delivery was not observed.

Figure 5:
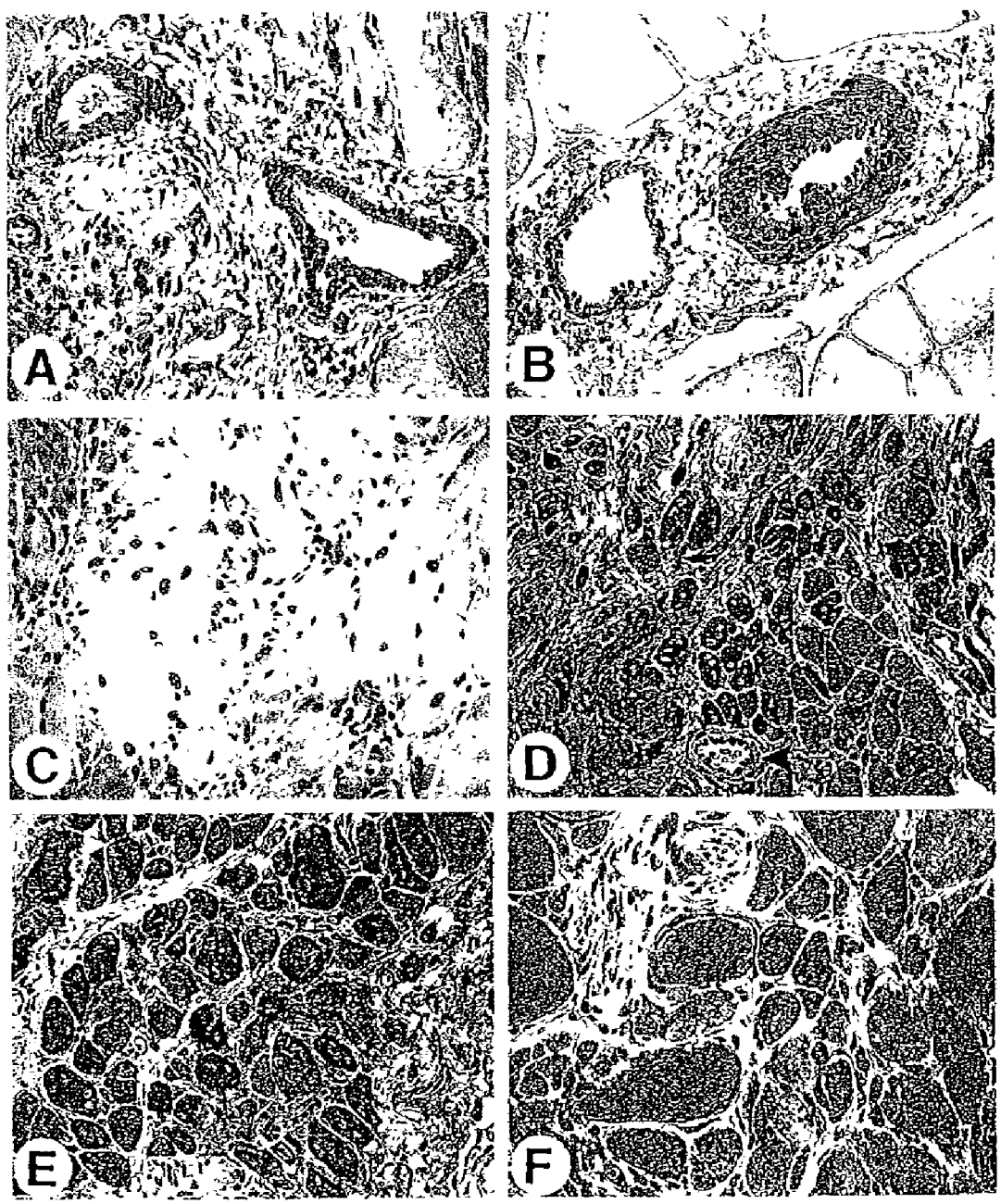
FIG. 5, panels A-F, arc micrographs showing alpha-actin and N-CAM expression following FGF gene delivery. Excisional defects were created in rat quadriceps muscles, and then injected with either 1 mg of $DNA_{FGF2}$ (panels A & D), 1 mg of $DNA_{FGF6}$ (panel B & E), or 60 μg of FGF2 protein (panels C & F). All treatments were formulated in a 1% collagen-1% gelatin admixture. At day 21 post-treatment, treatment sites were harvested and stained to detect either α-actin (A-C) or N-CAM (D-F) expression. The FIG. 6, panels A-F, are micrographs showing the influence of wounding on matrix remodeling and transgene expression. Rat rectus muscles were directly injected with $DNA_{FGF2}$ formulated in 1% collagen-1% gelatin (A-D), using a 27 g needle so as to induce minimal tissue injury. Alternatively, excisional defects were created in rectus muscles using a 3 mm biopsy punch, and this same material delivered directly into wound sites (E-F). At day 2 (C), 4 (E), 8 (D&F), or 21 (A&B) post-treatment, wound sites were harvested and stained according to Masson's trichrome procedure (A&B), or immunohistochemically to detect human FGF2 transgene expression. Arrowheads point to fibroblasts, arrows to blood vessels. Original magnifications 400×(A & C-E) or 1,000× (B&F).

In order to quantify arteriogenic responses, anti-α-actin immunohistochemistry followed by morphometric analyses was used to calculate the total arteriole wall area within gene delivery sites. Anti-α-actin staining confirmed that arterioles present in FGF2 or FGF6 gene-treated wounds contained tunica media layers comprised of numerous smooth muscle cells (FIG. 5). Morphometric analyses showed that, compared to luciferase gene-treated sites, FGF2-treated sites contained an average of 6.9-fold more arterioles as determined by total wall area (P<0.04, Table 1). Similarly, FGF6 gene delivery led to a 9.3-fold increase over controls (P<0.02). By contrast, although FGF2 protein-treated sites showed a trend towards enhanced arteriole area, this did not reach the level of statistical significance (Table 1), and immunohistochemistry failed to reveal prominent arterioles similar to those seen at gene-treated sites (FIG. 5).

TABLE 1

| Group | Arteriole Wall Area ($\mu m^2$) |
|---|---|
| $DNA_{Luc}$ GAM | 212 ± 27 |
| $DNA_{FGF2}$ GAM | 1,471 ± 437 * |
| $DNA_{FGF6}$ GAM | 1,987 ± 788 ** |
| FGF2 Protein | 462 ± 68 |

Arteriole development following FGF gene or protein delivery. Plasmid DNA encoding either FGF2, FGF6, or luciferase were formulated in a 1% collagen-1% gelatin admixture and delivered to rectus muscle defects as 1 mg DNA/site. FGF2 protein was also prepared in this same vehicle and delivered as 60 µg/site. At 21 days post-treatment, treatment sites were harvested and processed for anti-α-actin immunohistochemistry and morphometric analyses as described in Materials,in order to determine the total arteriole wall area per delivery site (n = 6). Data presented as means ± SEM.
* P = 0.01 vs. $DNA_{Luc}$ GAM;
** P = 0.02 vs. $DNA_{Luc}$ GAM.

Figure 6:
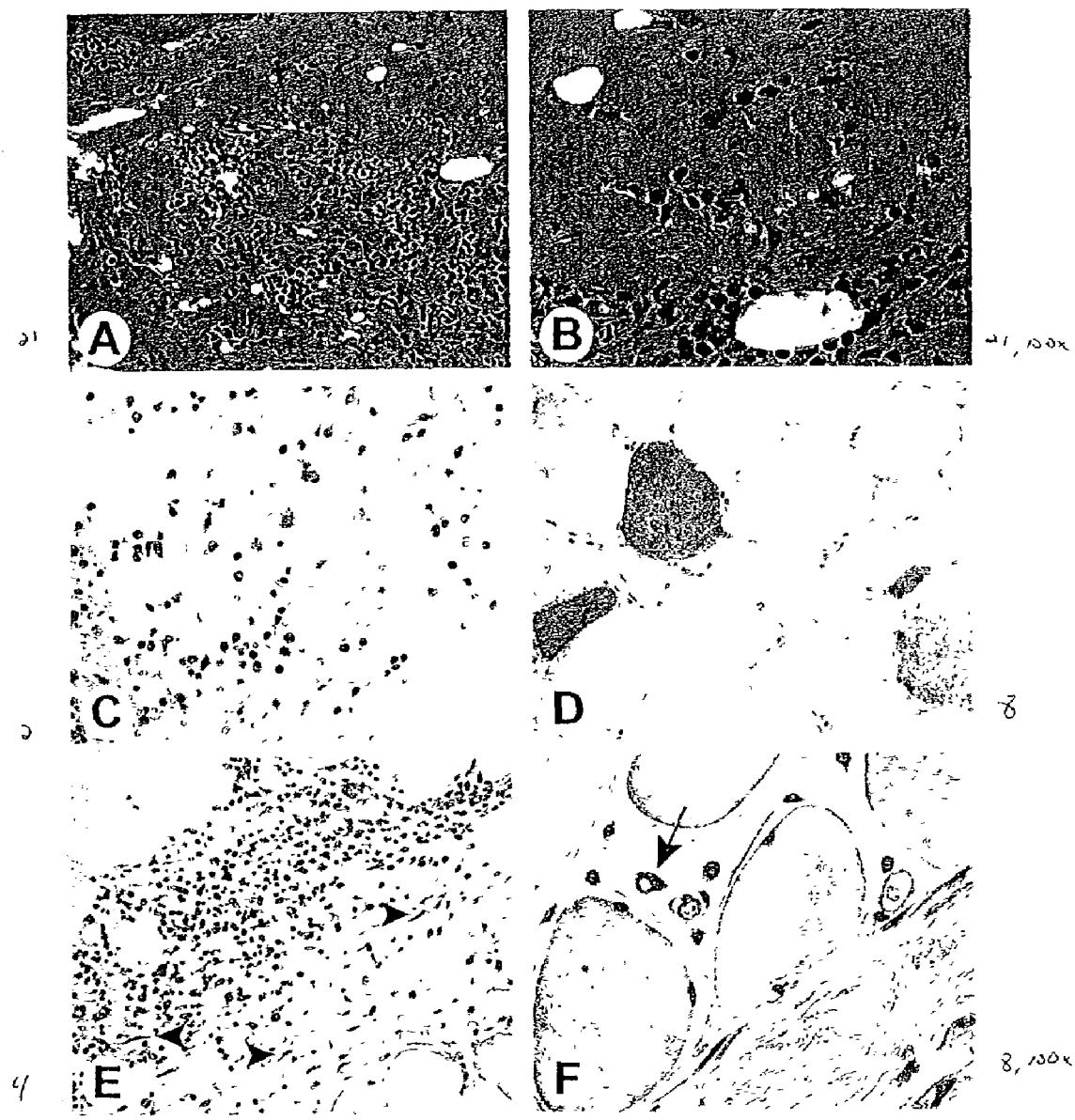

As a final study group, collagen/gelatin-formulated $DNA_{FGF2}$ was also delivered to intact muscles, without the prior creation of a surgical wound. At 21 days post-delivery, these sites appeared very similar to $DNA_{Luc}$ treatment sites, containing considerable collagen-gelatin matrix with little neovascularization and no higher order vessels such as muscular arterioles (FIG. 6). Accordingly, collagen formulations of either FGF2 or FGF6 genes induce repair processes marked by both angiogenesis and arteriogenesis, and that these responses are dependent both upon FGF transgene delivery and the induction of a wound repair response.

Example 6

FGF Gene Delivery to Skeletal Muscle Wounds Induces Myocyte Regeneration

As noted in the Examples above, it appeared that by day 21 more skeletal muscle bundles were interspersed within muscle wound sites following FGF gene delivery as compared to control gene delivery (see FIG. 5). Reasoning that this could represent enhanced muscle repair following FGF gene delivery, the expression of N-CAM within treated muscles was examined, as this molecule is upregulated on both proliferating and regenerating myocytes. Although a basal level of N-CAM expression was observed at all injury sites, as would be expected from normal muscle repair following wounding, expression was considerably more intense and widely distributed at FGF2 and FGF6 gene-treated sites as compared to either luciferase gene or FGF2 protein-treated sites. In addition, those muscle bundles expressing the highest levels of N-CAM were smaller in size, and contained prominent centrally located nuclei, markers characteristic of regenerating skeletal muscle. Finally, N-CAM expression was also noted on the endothelial lining of arterioles, suggesting that this molecule may also be a marker of developing endothelium.

Morphometric analyses were also used to confirm these qualitative assessments (FIG. 5). Delivery of $DNA_{FGF2}$ enhanced myocyte N-CAM expression by 9.1-fold (P<0.01), and $DNA_{FGF6}$ delivery enhanced expression 8.9-fold (P<0.01), as compared to luciferase gene treatment (Table 2). FGF2 protein induced a trend towards enhanced N-CAM expression, however as with arteriole area this did not rise to the level of statistical significance. Taken together with their ability to induce muscular arteriole formation, these results indicate that collagen-immobilized FGF genes enhance tissue repair at skeletal muscle wound sites.

TABLE 2

| Group | Area of N-CAM expression ($\mu m^2$) |
|---|---|
| $DNA_{Luc}$ GAM | 2,147 ± 700 |
| $DNA_{FGF2}$ GAM | 19,349 ± 6,487* |
| $DNA_{FGF6}$ GAM | 19,061 ± 4,995* |
| FGF2 Protein | 6,677 ± 2,523 |

N-CAM expression following FGF gene or protein delivery. Plasmid DNA encoding either FGF2, FGF6, or firefly luciferase were formulated in a collagen-gelatin admixture and delivered to rectus muscle wounds as 1 mg DNA/site FGF2 protein was also prepared in this same vehicle and delivered as 60 µg/site. At 21 days post-treatment, muscle defects were harvested and processed for anti-N-CAM immunohistochemistry and morphometric analyses as described in Materials, in orderto determine the total area of N-CAM expression per delivery site (n = 6). Data presented as means ± SEM.
*P = 0.01 vs. $DNA_{Luc}$ GAM.

Example 9

An In Vivo Model for the Study of the Effect of Matrix-Gene Delivery on Repair of Articular Cartilage Defects An in vivo model for cartilage repair is a full-thickness articular cartilage defect in the rabbit (Amiel et al., 1985, J. Bone Joint Surg. 67A:911 and as described in U.S. Pat. No. 5,972,385, hereby incorporated in their entirety by reference). Defects measuring approximately 3.7 mm in diameter and 5 mm deep defect are created in the center of the medial femoral condyles of adult male New Zealand white rabbits. The defects are then either filled with matrix expressing a gene of interest or left unfilled as controls. The defects are evaluated morphologically and histologically at 6 and 12 weeks.

Example 10

An In Vivo Model of Repair of Ischemic Heart Disease

A porcine model of myocardial ischemia that mimics clinical coronary artery disease is used-with the matrices of the present invention, as described in U.S. Pat. No. 5,792,453, incorporated herein by reference in its entirety. Briefly, placement of an ameroid constrictor around the left circumflex (LCx) coronary artery results in gradual complete closure (within 7 days of placement) with minimal infarction (1% of the left ventricle, 4±1% of the LCx bed) (Roth, et al. Circulation 82:1778, 1990, Roth, et al. Am J Physiol 235:H1279, 1987, White, et al. Circ Res 71:1490, 1992, Hammond, et al. Cardiol 23:475, 1994, and Hammond, et al. J Clin Invest 92:2644, 1993). Myocardial function and blood flow are normal at rest in the region previously perfused by the occluded artery (referred to as the ischemic region), due to collateral vessel development, but blood flow reserve is insufficient to prevent ischemia when myocardial oxygen demands increase. Thus, the LCx bed is subject to episodic ischemia, analogous to clinical angina pectors. Collateral vessel development and flow-function relationships are stable within 21 days of ameroid placement, and remain unchanged for four months (Roth, et al. Circulation 82:1778, 1990, Roth, et al. Am J Physiol 235:H1279, 1987, White, et al. Circ Res 71:1490, 1992). It has been documented by telemetry that animals have periodic ischemic dysfunction in the bed at risk throughout the day, related to abrupt increases in heart rate during feeding, interruptions by personnel, etc. Thus, the model has a bed with stable but inadequate collateral vessels, and is subject to periodic ischemia. Another distinct advantage of the model is that there is a normally perfused and functioning region (the LAD bed) adjacent to an abnormally perfused and functioning region (the LCx bed), thereby offering a control bed within each animal.

Myocardial contrast echocardiography is used to estimate regional myocardial perfusion. The contrast material is composed of microaggregates of galactose and increases the echogenicity (whiteness) of the image. The microaggregates distribute into the coronary arteries and myocardial walls in a manner that is proportional to blood flow (Skyba, et al. Circulation 90:1513-1521, 1994). It has been shown that peak intensity of contrast is closely correlated with myocardial blood flow as measured by microspheres (Skyba, et al. Circulation 90:1513-1521, 1994). To document that the echocardiographic images employed in the present invention are accurately identifying the LCx bed, and that myocardial contrast echocardiography is used to evaluate myocardial blood flow, a hydraulic cuff occluder is placed around the proximal LCx adjacent to the ameroid.

When animals are sacrificed, the hearts are perfusion-fixed (glutaraldehyde, physiological pressures, in situ) in order to quantitate capillary growth by microscopy. PCR is used to detect angiogenic protein DNA and mRNA in myocardium from animals that receive gene transfer. In addition, two weeks after gene transfer, myocardial samples from control lacZ-infected animals can show substantial .beta.-galactosidase activity on histological inspection. Finally, using a polyclonal antibody to an angiogenic protein, angiogenic protein expression in cells and myocardium from animals that receive gene transfer is measured.

The strategy for therapeutic studies includes the timing of matrix/transgene delivery, the route of administration of the matrix/transgene, and choice of the matrix/angiogenic gene. A more detailed description of the procedure follows.

Animals used for the study of eschemic heart disease are domestic pigs (30-40 kg). A left thoracotomy is performed under sterile conditions for instrumentation. (Hammond, et al. *J Clin Invest* 92:2644-2652, and Roth, et al. *J Clin Invest* 91:939-949, 1993). Catheters are placed in the left atrium and aorta, providing a means to measure regional blood flow, and to monitor pressures. Wires are sutured on the left atrium to permit ECG recording and atrial pacing. Finally, an ameroid is placed around the proximal LCx. After a stable degree of ischemia develops, the treatment group receives matrix including a gene or genes of interest according to the present invention (e.g., FGF, VEGF, TGF, TNF-α, HGF, PDGF), driven by the appropriate promoter. Control animals receive gene transfer with an construct that includes a reporter gene, such as lacZ, driven by the same promoter.

Studies are initiated 35±3 days after ameroid placement, at a time when collateral vessel development and pacing-induced dysfunction are stable (Roth, et al. *Am J Physiol* 253: H1279-1288, 1987, and Roth, et al. *Circulation* 82:1778-1789). Conscious animals are suspended in a sling and pressures from the LV, LA and aorta, and electrocardiogram are recorded in digital format on-line (at rest and during atrial pacing at 200 bpm). Two-dimensional and M-mode images are obtained using for example a Hewlett Packard ultrasound imaging system. Images are obtained from a right parasternal approach at the mid-papillary muscle level and recorded on VHS tape. Images are recorded with animals in a basal state and again during right atrial pacing (HR=200 bpm). These studies are performed one day prior to gene transfer and repeated 14±1 days later. Echocardiographic measurements are made using standardized criteria (Sahn, et al. Circulation 58:1072, 1978). End-diastolic wall thickness (EDWTh) and end-systolic wall thickness (ESWTh) are measured from 5 continuous beats and averaged. Percent wall thickening (% VVTh) is calculated. Data are analyzed without knowledge of which matrix/gene the animals receive. To demonstrate reproducibility of echocardiographic measurements, animals are imaged on two consecutive days.

35±3 days after ameroid placement, well after ameroid closure, but before gene transfer, contrast echocardiographic studies are performed using the contrast material (Levovist) which is injected into the left atrium during atrial pacing (200 bpm). Studies are repeated 14±1 days after gene transfer. Peak contrast intensity is measured from the video images using for example, a computer-based video analysis program (Color Vue II, Nova Microsonics, Indianapolis, Ind.), that provides an objective measure of video intensity. The contrast studies are analyzed without knowledge of which gene the animals had received.

At completion of the study, animals are anesthetized and midline thoracotomy performed. The brachycephalic artery is isolated, a canula inserted, and other great vessels ligated. The animals receive intravenous heparin (10,000 IU) and papaverine (60 mg). Potassium chloride is given to induce diastolic cardiac arrest, and the aorta cross-clamped. Saline is delivered through the brachycephalic artery cannula (120 mmHg pressure), thereby perfusing the coronary arteries. Glutaraldehyde solution (6.25%, 0.1 M cacodylate buffer) is perfused (120 mmH pressure) until the heart is well fixed (10-15 min). The heart is then removed, the beds identified using color-coded dyes injected anterograde through the left anterior descending (LAD), left circumflex (LCx), and right coronary arteries. The ameroid is examined to confirm closure. Samples taken from the normally perfused and ischemic regions are divided into thirds and the endocardial and epicardial thirds are plastic-imbedded. Microscopic analysis to quantitate capillary number is conducted as previously described (Mathieu-Costello, et al. Am J Physiol 359:H204, 1990). Four 1 pm thick transverse sections are taken from each subsample (endocardium and epicardium of each region) and point-counting is used to determine capillary number per fiber number ratio at 400×magnification. Twenty to twenty-five high power fields are counted per subsample. Within each region, capillary number to fiber number rations are similar in endocardium and epicardium so the 40-50 field per region are averaged to provide the transmural capillary to fiber number ratio.

To establish that improved regional function and blood flow results from transgene expression, PCR and RT-PCR are used to detect transgenic DNA and mRNA in myocardium from animals that had received gene transfer.

Finally, using a polyclonal antibody directed against the protein expressed from the gene or genes of interest, protein expression is demonstrated 48 hours as well as 14±1 days after gene transfer in cells and myocardium from animals that receive gene transfer.

Example 11

A Swine Model of Transmyocardial Revascularization

Farm swine (~50 kg) are anesthetized, intubated, and maintained on inhaled isoflurane. Left thoracotomies are performed through the fifth intercostal space, hearts exposed by opening the pericardium, and six controlled injuries are placed in anterior and posterolateral reions of the left ventricle. This is accomplished using 5 different mechanical devices and a pulsed homium:yttrium-aluminum-garnet laser. The resulting injuries are ~7 mm wide, 5 mm deep and 4 cm apart. Matrix-DNA treatments are injected directly into TMR channels using an automated syringe delivery system. Finally, animals are closed, allowed to recover from anesthesia, and housed for either 3 or 6 weeks, at which time myocardial tissue is sampled and processed for paraffin embedding. For routine morphological assessment, paraffin sections are stained according to Masson's trichrome procedure. Expression of the gene or genes of interest can also be measured using techniques known to skilled artisans, such as immunohistochemistry and in situ PCR.

From the foregoing it will be appreciated that, although specific embodiments of the invention have been described herein for purposes of illustration, various modifications may be made without deviating from the spirit and scope of the invention. Accordingly, the invention is not limited except as by the appended claims. In addition, all patents, patent applications, and other references referred to herein are incorporated by reference in their entirety.

What is claimed is:

1. A method for treating a tissue injury associated with ischemic heart disease comprising directly implanting a matrix-gene composition comprising an angiogenic gene operably linked to a promoter and a biocompatible matrix capable of supporting cellular ingrowth into an injured ischemic region of a heart, wherein the ischemic region comprises myocardial tissue contacting a pericardial fluid space, wherein the biocompatible matrix comprises collagen, and wherein the composition transfers the angiogenic gene to cells associated with the fluid space and induces an angiogenic response in the tissue, thereby stimulating blood vessel formation in the ischemic region of the heart.

2. The method of claim 1 wherein the angiogenic gene is an FGF gene, a VEGF gene, a TGF gene, a TNFα gene, an HGF gene, or a PDGF gene.

3. The method of claim 1 wherein the biocompatible matrix is a collagen, hydroxyapatite, lactic acid polymer, or fibrin matrix.

* * * * *

UNITED STATES PATENT AND TRADEMARK OFFICE
CERTIFICATE OF CORRECTION

PATENT NO. : 7,534,774 B2 Page 1 of 1
APPLICATION NO. : 10/264284
DATED : May 19, 2009
INVENTOR(S) : Barbara A. Sosnowski et al.

It is certified that error appears in the above-identified patent and that said Letters Patent is hereby corrected as shown below:

Title Page Item 56:

U.S. PATENT DOCUMENTS:

The reference "4,972,385 11/1990 Teel" should read --5,972,385 10/1999 Liu et al. 424/486--.

Title Page Item 56:

FOREIGN PATENT DOCUMENTS:

The reference "WO WO97/00201 1/1987" should read as --WO WO87/00201 1/1987--.

Signed and Sealed this

First Day of June, 2010

David J. Kappos
*Director of the United States Patent and Trademark Office*